(12) United States Patent
Friedman et al.

(10) Patent No.: US 11,439,587 B2
(45) Date of Patent: Sep. 13, 2022

(54) INJECTABLE IMPLANTS

(71) Applicant: YISSUM RESEARCH DEVELOPMENT COMPANY OF THE HEBREW UNIVERSITY OF JERUSALEM LTD., Jerusalem (IL)

(72) Inventors: Michael Friedman, Jerusalem (IL); David Kirmayer, Maale Adumim (IL); Rami Mosheiff, Jerusalem (IL); Jacob Rachmilewitz, Modi'in (IL); Amal Khoury, Jerusalem (IL); Doron Steinberg, Jerusalem (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 102 days.

(21) Appl. No.: 16/335,471

(22) PCT Filed: Sep. 19, 2017

(86) PCT No.: PCT/IL2017/051060
§ 371 (c)(1),
(2) Date: Mar. 21, 2019

(87) PCT Pub. No.: WO2018/055615
PCT Pub. Date: Mar. 29, 2018

(65) Prior Publication Data
US 2019/0298649 A1 Oct. 3, 2019

Related U.S. Application Data

(60) Provisional application No. 62/398,016, filed on Sep. 22, 2016.

(51) Int. Cl.
*A61K 9/00* (2006.01)
*A61K 31/09* (2006.01)
(Continued)

(52) U.S. Cl.
CPC ............ *A61K 9/0024* (2013.01); *A61K 31/09* (2013.01); *A61K 31/155* (2013.01);
(Continued)

(58) Field of Classification Search
CPC .... A61K 9/0024; A61K 31/09; A61K 31/155; A61K 31/192; A61K 31/366;
(Continued)

(56) References Cited

U.S. PATENT DOCUMENTS 5,340,849 A 8/1994 Dunn et al.
5,599,552 A 2/1997 Dunn et al.
(Continued)

FOREIGN PATENT DOCUMENTS

| WO | 2010/079496 | 7/2010 |
|----|-------------|--------|
| WO | 2012/101242 | 8/2012 |
| WO | 2013/163705 | 11/2013 |

OTHER PUBLICATIONS

Gupta et al, An Overview of Polymethacrylate Polymers in Gastroretentive Dosage Forms, Open Pharmaceutical Sciences Journal, 2015, 2, pp. 31-42. (Year: 2015).*
(Continued)

*Primary Examiner* — Trevor Love
(74) *Attorney, Agent, or Firm* — Nixon & Vanderhye PC

(57) ABSTRACT

Provided herein injectable implant compositions useful for acceleration of bone fracture healing, treatment of dental or oral pathologies, and controlled drug delivery.

23 Claims, 4 Drawing Sheets

(51) Int. Cl.
  A61K 31/155    (2006.01)
  A61K 31/192    (2006.01)
  A61K 31/366    (2006.01)
  A61K 31/4164   (2006.01)
  A61K 31/4425   (2006.01)
  A61K 31/65     (2006.01)
  A61K 47/02     (2006.01)
  A61K 47/32     (2006.01)
  A61K 47/38     (2006.01)

(52) U.S. Cl.
  CPC .......... *A61K 31/192* (2013.01); *A61K 31/366* (2013.01); *A61K 31/4164* (2013.01); *A61K 31/4425* (2013.01); *A61K 31/65* (2013.01); *A61K 47/02* (2013.01); *A61K 47/32* (2013.01); *A61K 47/38* (2013.01)

(58) Field of Classification Search
  CPC ............ A61K 31/4164; A61K 31/4425; A61K 31/65; A61K 47/02; A61K 47/32; A61K 47/38
  See application file for complete search history.

(56) References Cited

U.S. PATENT DOCUMENTS

| | | | |
|---|---|---|---|
| 6,022,554 A * | 2/2000 | Lee | A61K 9/0024 424/423 |
| 2008/0069878 A1 * | 3/2008 | Venkatesh | A61K 9/5042 424/468 |
| 2010/0035904 A1 * | 2/2010 | Sun | A61P 25/20 514/270 |

OTHER PUBLICATIONS

International Search Report for PCT/IL2017/051060, dated Jan. 18, 2018, 4 pages.
Written Opinion of the ISA for PCT/IL2017/051060, dated Jan. 18, 2018, 6 pages.
T. Srichan et al., Designing Solvent Exchange-Induced In Situ Forming Gel from Aqueous Insoluble Polymers as Matrix Base for Periodontitis Treatment, AAPS PharmSciTech, vol. 18, No. 1, Jan. 2017, pp. 194-201.
Office Action issued in EP Appln. No. 17 791 465.2 dated Jul. 6, 2020.
Borude et al., "Formulation and Evaluation of Dental Implant of Moxifloxacin HCL for the Treatment of Periodontitis" *International Journal of Pharmacy and Biological Sciences*, vol. 3, No. 4: 49-55 (2013).
Chen et al., "Brittle and ductile adjustable cement derived from calcium phosphate cement/polyacrylic acid composites" *Dental Materials*, vol. 24: 1616-1622 (2008).
Ismail et al., "In Situ Gel Formulations for Gene Delivery: Release and Myotoxicity Studies" *Pharmaceutical Development and Technology*, vol. 5, No. 3: 391-397 (2000).
Mahadlek et al., "Metrodidazole In Situ Forming Eudragit RS Gel Comprising Different Solvents" *Key Engineering Materials*, vol. 659: 13-18 (2015).

* cited by examiner

INJECTABLE IMPLANTS

This application is the U.S. national phase of International Application No. PCT/IL2017/051060 filed 19 Sep. 2017, which designated the U.S. and claims the benefit of U.S. Application No. 62/398,016 filed 22 Sep. 2016, the entire contents of each of which are hereby incorporated by reference.

FIELD OF THE INVENTION

The present invention relates to injectable implants useful, inter alia, for accelerated fracture healing. The injectable implants may comprise an active agent for controlled release, e.g. in the perifractural space, in oral or dental cavities, or for systemic delivery. Methods of treatment of bone fractures by administering the injectable implants to the perifractural space and the uses of the injectable implants for the treatment of the bone fractures, particularly in the accelerated fracture healing, are also provided. Methods of treatment of systemic diseases by administering the injectable implants to a patient in need thereof, and the uses of the injectable implants for the treatment of the various systemic conditions, are also provided. Methods of treatment of an oral condition by administering the injectable implants to a patient in need thereof, and the uses of the injectable implants for the treatment of the various oral conditions, are also provided.

BACKGROUND

Bone fractures are a common complication of various traumatic events and several pathological bone conditions. Despite the great regenerative potential of the bone, it may sometimes be insufficient and bone loss may ensue following trauma, tumor resection, infection and skeletal abnormalities. Critical defects may be predictive of non-union, and a rule of thumb is that a defect that is larger than 1.5-2 times the diaphysis diameter may be considered critical. Various research strategies exist to prevent and combat critical bone defects; many approaches include barrier membranes approach, scaffolds, composite materials, hydrogels, grafts, and mesenchymal stem cells (MSCs) delivery. MSCs constitute a heterogeneous multipotent adult stem cell population with similar characteristics and are distributed in several tissues. They have the ability to differentiate into a wide range of cell types such as chondroblasts, lipoblasts and osteoblasts. Nevertheless skeletal postnatal stem cells may also be involved in bone regeneration processes.

A guided bone regeneration process with a barrier membrane comprising ammonio-methacrylate copolymer, type A, USP, is described in PCT publication WO/2010/079496. The membrane supports the adhesion, proliferation and osteoblastic differentiation of human MSCs, and is capable of controlled delivery of simvastatin.

The drawback of implants, such as membranes is that they need to be inserted by surgery. Moreover, the need for surgery usually outweighs the benefits of fracture healing acceleration in non-critical fractures. Some injectable implants (solidifying compositions) of poly-lactic-co-glycolic acid are described, inter alia, in U.S. Pat. Nos. 5,340,849 and 5,599,552. However, the injectable implants of poly-lactic-co-glycolic acid do not support the growth of MSCs. Injectable gels comprising ammonio-methacrylate copolymer, type B, USP, were recently described in T. Srichan and T. Phaechamud, AAPS PharmSciTech, (2016) 1-8; however the gels did not maintain shape and disintegrated.

There is a need to provide barrier implant compositions suitable for the application, inter alia, in non-critical bone defects. There is a need to provide the perifractural barrier implant compositions that could be administered by injection. There is a further need to provide the perifractural barrier implant composition that supports the attachment, the proliferation and/or the osteoblastic differentiation of stem cells. There is a further need to provide the perifractural barrier implant compositions comprising active agents for the acceleration of bone fracture healing.

Additionally, there is a need to provide injectable implant compositions for controlled release of drugs for extended time intervals, preferably retaining the shape for prolonged intervals.

The present invention solves the problems by providing rapidly solidifying injectable implant compositions, e.g. fracture barrier implants, comprising polymethacrylate copolymers, preferably charge-bearing polymers, preferably positively charged polymers.

SUMMARY OF THE INVENTION

In one aspect there is provided a composition of an injectable barrier implant for the acceleration of bone healing. The injectable barrier implant composition comprises polymethacrylate(s) that are either insoluble or not instantly soluble in water at physiological pH, e.g. pharmaceutical polymethacrylates as defined below, and a suitable water-soluble organic solvent. The water-soluble organic solvent has a high solubility in water; preferably, the water-soluble organic solvent is miscible with water in all proportions. The water-soluble organic solvent leaves the injectable implant composition upon contact with aqueous medium, e.g. upon injection, thereby effecting the solidification of the polymers of the implant. The polymethacrylates compositions are formulated to bear a positive charge or to assume the positive charge upon solidification, by the use of appropriate polymers and additives. The injectable implant composition may further comprise additional polymers, co-solvents, additives, and polyvalent cation sources. It has been unexpectedly found that polymethacrylates may be combined with certain additives to improve the mechanical properties of the solidified residue, particularly with a salt. It has further been unexpectedly found that the polymers that are known as incompatible may coexist in a solution in the presence of N-methyl pyrrolidone, as a solvent or a co-solvent. The solidified residues of these solutions possess exceptional mechanical properties and decreased degradation. It has further been unexpectedly found that the injectable implants may be produced from lower concentration of the polymer when combined with additional polymers or additives. Moreover, it has been found that water-soluble polymers may be used to control the porosity of the implants.

In a further aspect of the invention, provided is a composition of a medicated injectable barrier implant. The medicated injectable barrier implant is preferably the injectable barrier implant further comprising at least one bone-active ingredient. Upon solidification, the bone-active ingredient is released from the implant into the ambient aqueous medium. The release of the bone-active agent is controlled by the composition of the solidified implant.

In an additional aspect of the invention there is provided a kit for extemporaneous preparation of the composition or of the medicated composition according to the invention, the kit comprising at least two separate containers comprising each at least one solvent or solution or at least one powder, e.g. polymethacrylate powder, and/or an additive powder, and/or a drug powder, such that upon aseptic addition of the solvent or solution to the powder a composition or a medicated composition of the invention is obtained.

In an additional aspect provided a method of treatment of bone fractures by administering to the patient in need a dose of composition or of medicated composition of the invention, perifracturally. The administration of the composition or of the medicated composition may be preceded or followed by administration of auxiliary compositions, comprising at least one of a drug, a divalent ion, a cell, and/or an injectable gel, e.g. a thermosensitive polymer solution.

In a further aspect of the invention, provided is a composition of a medicated injectable implant. The medicated injectable implant compositions comprise materials as injectable barrier implants, but there is no need to bear a positive charge or to assume the positive charge upon solidification. The injectable implant composition may further comprise additional polymers, co-solvents, additives, and polyvalent cation sources. Depending on the intended use, the injectable implants may comprise polymers and materials that are either degradable or non-degradable.

In an additional aspect provided a method of treatment of systemic diseases by administering to the patient in need at least one dose of a medicated composition of the invention. In an additional aspect provided a method of treatment of oral pathologies by administering to the patient in need at least one dose of a medicated composition of the invention.

An injectable implant composition of the invention may comprise a polymethacrylate selected from the group consisting of methacrylic acid copolymers, ammonio-methacrylate copolymers, amino methacrylate copolymers, and mixtures thereof, an injectable solvent capable of dissolving said polymethacrylate, an additive selected from a salt or a mineral, and optionally a pharmaceutically active agent. The injectable solvent is preferably soluble in or miscible with water, and may be selected from aprotic solvents, polyols, and organic acid esters. Examples of suitable injectable solvents may be selected from the group consisting of N-methyl pyrrolidone, dimethyl sulfoxide, polyethylene glycol with molecular weight between 300 and 4000, propylene glycol, glycerine, triethyl citrate, and combinations of at least two of the above.

The suitable additive may be calcium-containing salt or mineral, preferably the salt is calcium chloride, and/or the mineral is hydroxyapatite. The implant may further comprising a cosolvent, or water.

The methacrylic acid copolymer may be selected from copolymers of methacrylic acid and methyl methacrylate, and copolymers of methacrylic acid and ethyl acrylate. The ammonio methacrylate copolymer may be a copolymer of ethyl acrylate, methyl methacrylate and trimethylammonioethyl methacrylate chloride. The amino methacrylate copolymer may be a copolymer of dimethylaminoethyl methacrylate, butyl methacrylate, and methyl methacrylate. The injectable implant may further comprise at least one further polymer, selected from the group consisting of a polyester, a cellulose derivative, polyvinyl pyrrolidone, a polyethylene glycol, a polyethylene oxide, and a poloxamer. The suitable cellulose derivative is methyl cellulose, hypromellose, and hydroxypropyl cellulose.

The injectable implant may comprise a pharmaceutically active agent, preferably a bone-active agent, further preferably the bone-active agent is simvastatin. The injectable implant may generally comprise a pharmaceutically active agent that may be selected from the group consisting of antibiotics, antifungals, antivirals, antineoplastics, antiepileptics, antiparkinsonics, and hormones. Alternatively, a pharmaceutically active agent that may be selected from an antiseptic, an antibiotic, an antibiofilm agent, an anti-quorum sensing agent, and a non-steroid anti-inflammatory agent. Preferably, the antiseptic may be cetyl pyridinium chloride, and non-steroid anti-inflammatory agent is ibuprofen.

Preferably, the injectable implant may comprise a copolymer of ethyl acrylate, methyl methacrylate and trimethylammonioethyl methacrylate chloride as a polymethacrylate, calcium chloride as an additive, water, a pharmaceutically active agent, and N-methyl pyrrolidone as a solvent. Further preferably, the injectable implant may comprise a mixture of a first polymethacrylate which is a copolymer of ethyl acrylate, methyl methacrylate and trimethylammonioethyl methacrylate chloride, and a second polymethacrylate which is selected from a copolymer of methacrylic acid and methyl methacrylate, a copolymer of methacrylic acid and ethyl acrylate, and a mixture thereof; calcium chloride as an additive; water; a pharmaceutically active agent; and N-methyl pyrrolidone as a solvent.

In an alternative embodiment, the injectable implant composition may comprise a mixture of at least two polymethacrylates, a first polymethacrylate selected from copolymers of methacrylic acid and methyl methacrylate, and copolymers of methacrylic acid and ethyl acrylate, a second polymethacrylate which is a copolymer of dimethylaminoethyl methacrylate, butyl methacrylate, and methyl methacrylate, and an injectable solvent capable of dissolving said polymethacrylate copolymers.

In a further embodiment, provided a method of accelerating a bone fracture healing in a patient in need thereof by administering perifracturally an injectable implant composition comprising a copolymer of ethyl acrylate, methyl methacrylate and trimethylammonioethyl methacrylate chloride, an injectable solvent capable of dissolving said copolymer, an additive selected from a salt or a mineral, and optionally a bone active agent. Preferably, the injectable implant composition further comprises a copolymer of methacrylic acid and methyl methacrylate, a copolymer of methacrylic acid and ethyl acrylate, or a mixture thereof.

In a further embodiment, provided a method of treatment of a dental or an oral pathology in a patient in need thereof by administering to said patient an injectable implant composition comprising a polymethacrylate selected from the group consisting of methacrylic acid copolymers, ammonio-methacrylate copolymers, amino methacrylate copolymers, and mixtures thereof, an injectable solvent capable of dissolving said polymethacrylate, an additive selected from a salt or a mineral, and a pharmaceutically active agent. Preferably, the pharmaceutically active agent selected from an antiseptic, an antibiotic, an antibiofilm agent, an anti-quorum sensing agent, and a non-steroid anti-inflammatory agent.

In a further embodiment, provided a method of treatment of a pathology in a patient in need thereof by administering to said patient intramuscularly, subcutaneously or intraperitoneally an injectable implant composition comprising a polymethacrylate selected from the group consisting of methacrylic acid copolymers, ammonio-methacrylate copolymers, amino methacrylate copolymers, and mixtures thereof, an injectable solvent capable of dissolving said polymethacrylate, an additive selected from a salt or a mineral, and a pharmaceutically active agent.

DETAILED DESCRIPTION

Figure 1:
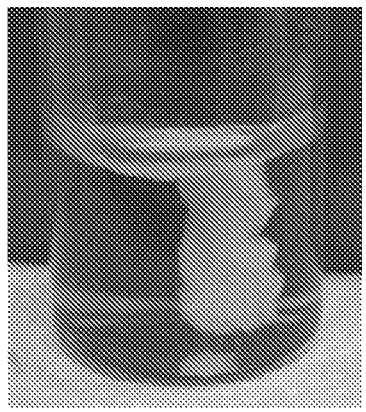
FIG. 1 demonstrates a photograph of a solidified residue from an injectable composition of one embodiment of the invention in a cross-linked gelatin gel.

"Perifractural"—as used herein the term is related to the vicinity of a bone fracture. The term should be preferably construed, unless the context dictates otherwise, the space directly adjacent and contiguous to the fracture. Similarly, the term "periossal" as used herein is related to the vicinity of a bone.

"Bone-active"—as used herein refers to a drug eliciting biological action by augmenting bone-fracture healing processes or interfering with pathologic processes of the bone.

"Adhering cells"—as used herein refers to the cell lines or to cells in a living organism that, when cultured in vitro, adhere to a suitable substrate, e.g. tissue culture dishes. Normally, the adhering cells produce upon attachment to the surface a typical spindle-like morphology on a perfect substrate, a rounded morphology on a sub-optimal substrate and cluster-like morphology on a poor substrate. Typically, as used herein the term interchangeably relates to mesenchymal stem cells and to surrogate cells as described herein below.

"Residue", or "solidified residue", and the like—as used interchangeably herein refers to the solid mass obtained by exposure of the compositions as described herein to aqueous medium. Preferably, the terms refer to the solidified implants as described herein.

The injectable barrier implants of the composition as described herein are useful for the acceleration of healing of bone fractures. Without being bound by theory, it is believed that the specific surface properties of the formed implant upon injection allow attachment and proliferation of stem cells and osteoblasts. It is further believed that the liquid nature of the injectable implant allows for better coverage of the fracture hematoma, and the osteoadhesive properties of the polymethacrylate polymers, as has been unexpectedly found by the inventors, that may interact with hydroxyapatite, provides for proper insulation of the fracture area and functions as barrier implant. It is further believed that unilateral exposure to the residual solvents of the applied composition may lead to negligible biological interaction with the bone healing process, unlike in scaffold-like injectable structures. It is further believed that the perifractural area may be advantageously modified prior to or following the administration of the implant composition. Finally, it is believed that the drug released from medicated compositions reaches the highest levels in the perifractural space and provides minimal systemic exposure.

Additionally, a medicated injectable implant may be used for systemic delivery of drugs to the circulation of the patient, upon a suitable injection, e.g. intramuscular, intraperitoneal, or into subcutaneous space.

The injectable implant composition comprises pharmaceutical polymethacrylates and a suitable water-soluble organic solvent. The suitable polymethacrylates are pharmaceutical polymers, e.g. as defined in the USP32-NF27 as aminomethacrylate copolymer, ammonio-methacrylate copolymers, type A and type B, and methacrylic acid copolymers, type A, type B and type C, or their equivalents. Chemically, the suitable polymethacrylates include copolymers of ethyl acrylate, methyl methacrylate and trimethylammonioethyl methacrylate chloride, e.g. in a ratio 1:2:0.2, or in a ratio 1:2:0.1, available in nominal MW 28,000-35,000 (identified in the USP-NF as ammonio-methacrylate copolymers, types A and B, respectively); copolymers of methacrylic acid and methyl methacrylate, e.g. in a ratio 1:1, or in a ratio 1:2, available in nominal MW 110,000-135,000 (identified in the USP-NF as methacrylic acid copolymers, types A and B, respectively); copolymers of methacrylic acid and ethyl acrylate, e.g. in a ratio 1:1, available in nominal MW 290,000-350,000 (identified in the USP-NF as methacrylic acid copolymer, type C); copolymers of dimethylaminoethyl methacrylate, butyl methacrylate, and methyl methacrylate, e.g. in a ratio of 2:1:1, available in nominal MW 45,000-50,000 (identified in the USP-NF as aminomethacrylate copolymer).

It can be readily perceived that the ammonio-methacrylate copolymers bear quaternary ammonium groups on a polymethacrylic backbone. The density of the quaternary ammonium groups is varied according to the need. The aminomethacrylate copolymer bears tertiary amine groups, and under neutral conditions the aminomethacrylate copolymers are usually insoluble and their amine residues ionize with positive charge at lower pH. The ammonio-methacrylate copolymers bear positive charge constitutively. The ammonium quaternary groups are usually coupled with a counter-ion, e.g. with a chloride. The methacrylic acid copolymers bear carboxylic acid residues; the density of the residues and the nature of inert residues may be varied according to the need. Under neutral conditions the methacrylic acid copolymers usually dissolve and their carboxylic residues ionize with negative charge. However, it has been unexpectedly shown that adhering cells can adhere also to the solidified surfaces of the methacrylic acid copolymers, particularly in presence of polyvalent, e.g. divalent, cations. Without being bound by theory it is believed that in presence of biological fluids the polymer surface assumes positive charge, particularly in presence of polyvalent cations.

The ammonio-methacrylates and methacrylic acid copolymers are known, e.g. under the trade name Eudragit™, ammonio-methacrylates pertaining to the grades RL (type A) or RS (type B), aminomethacrylate copolymer pertains to the grade E, and methacrylic acid copolymers pertaining to the grades L (type A), S (type B) and L100-55 (type C).

The injectable implant composition may comprise a combination of the polymethacrylates. It has been unexpectedly found that under certain conditions, such as solvents, additives, and others, the ammonio-methacrylates and/or aminomethacrylates, and methacrylic copolymers may be combined without the polymers precipitating in presence of one another. The combination of the polymethacrylates may be in a preferred solvent as described below. The ratio of the polymers in the combination may be dictated by the purpose of such combination, and may vary from 1:50 to 50:1, preferably between 1:10 and 10:1, more preferably between 1:3 and 3:1. The polymers may be combined to decrease the degradation rate of soluble methacrylatic copolymers. In such combination, it may be advantageous to utilize a methacrylic acid copolymer as the main polymer, and an ammonio-methacrylate or amino-methacrylate copolymer as an additional polymer. The preferable weight ratio in such combinations is between 1:1 and 10:1, for either polymer. The polymers may be combined to control the surface properties of the residue, and/or the pH at the surface and around the implantation site.

The injectable implant composition further comprises a water-soluble organic solvent. The solvent leaves the injectable implant composition upon contact with aqueous medium, e.g. upon injection, thereby effecting the solidification of the polymers of the implant. The water-soluble and water-miscible properties of the organic solvent are important for effecting the solidification of the polymers into an implant. The suitable solvents include, but not limited to, at least one of water-miscible aprotic solvents, e.g. N-methyl pyrrolidone (NMP), dimethyl sulfoxide (DMSO); polyols, e.g. polyethylene glycol (PEG) or alkoxy-PEG of molecular weight between 300-1000, glycerol, and organic esters, e.g. triethyl citrate. The term "alkoxy-PEG" includes low alkyl-coupled (e.g. methyl, or ethyl) polyethylene glycol chains, from either one or both ends. Certain solvents may be less suitable, such as diethyl phthalate, that dissolves the polymers but is not readily water-soluble/water-miscible, or propylene glycol, that is water-soluble and water-miscible, but does not readily dissolve the polymers in required concentrations. It has been unexpectedly found that several solvents do not dissolve the polymers adequately, and these include glycerine triacetate (triacetin), PEG 200, and liquid surfactants, e.g. polysorbate or sorbitan esters. The preferred solvents include NMP, DMSO and PEG-400.

Mixtures of suitable solvents or a suitable solvent and a less suitable solvent may be suitable, e.g. NMP and propylene glycol. When used in such mixtures, the preferred solvents are usually above 30% wt of the total solvent composition, preferably above 40% wt, most preferably above 50% wt. Generally, injectable solvents are exemplified but not limited to, PEG 300, PEG 400, ethanol, propylene glycol, glycerine, N-methyl pyrrolidone, dimethyl sulfoxide, dimethyl acetamide, pegylated castor oil, pegylated hydrogenated castor oil, d-alpha-tocopherol-PEG-1000-succinate, polysorbate 20, polysorbate 40, polysorbate 60, polysorbate 80, pegylated 12-hydroxystearic acid, sorbitan monooleate, poloxamers, fatty-acid esters of PEG 300, 400, and 1750, castor oil, corn oil, cottonseed oil, olive oil, peanut oil, peppermint oil, safflower oil, sesame oil, soybean oil, hydrogenated vegetable oils, hydrogenated soybean oil, medium-chain triglycerides, fatty acids, oleic acid, phospholipids, e.g. hydrogenated soy phosphatidyl choline, distearoyl phosphatidyl glycerine, 1-alpha-dimyristoyl phosphatidyl choline, and 1-alpha-dimyristoyl phosphatidyl glycerine.

The concentrations of the injectable polymers suitable for the composition may be determined by the solvent or a combination of solvents used, and may be readily determined according to the demonstrated procedures in the Examples section. Briefly, the composition is injected into or subjected to either aqueous medium, or an aqueous gel, and solidification is observed. When the concentration is below the needed, dispersion of the solidified polymer may be observed and slow solidification may be seen in an aqueous gel. Typically, depending on the solvent and other excipients used as described herein, the concentration of the polymers may be from about 10% wt to about 40% wt, preferably between 15% wt and 25% wt. It has been found that N-methyl pyrrolidone provides the lowest viscosity for these polymers at a given concentration.

The injectable implant composition may further comprise additional polymers, co-solvents, additives (additional excipients), and polyvalent cation sources. The additional polymers may affect the properties of the solidified implant, e.g. the rate of solidification, the hydrophilicity or hydrophobicity of the surface, the porosity and tortuosity of the pores, the pores' size, and general morphology of the solidified residue surface. The additional polymers include, but not limited to, at least one of PEG-4000 and higher MW PEGs, polyethylene oxides, povidone, copovidone, cellulose derivatives, e.g. methyl cellulose, hydroxypropyl cellulose, carboxymethyl cellulose, hypromellose, gelatin and/or a poloxamer. The suitable poloxamers include, but not limited to poloxamer 407, poloxamer 188, poloxamer 237, poloxamer 338 and poloxamer 124. The amount of the additional polymers may be determined according to the purpose of the polymer, and may generally be less than 50% wt of the solids content in the composition, preferably less than 30% wt, and further preferably less than 10% wt. The additional polymer may be dispersed or dissolved in the composition. It has been unexpectedly found that Methocel® polymers, e.g. hypromellose and methyl cellulose, may be combined with polymethacrylates in a common solution, and may assist in controlling a drug release rate from medicated implants. It has also been found that dispersed materials, e.g. hydroxyapatite, may assist in solidification of the injectable implant compositions. Additives may also be insoluble polymers in the solvent, e.g. polyethylene oxide polymers do not dissolve in NMP, yet do not interfere with solidification and assist in forming pores and/or regulating the viscosity of the medium inside the pores.

The co-solvents may facilitate the incorporation of the additional polymers and/or other excipients into the compositions. The co-solvents include, but not limited to, at least one of ethanol, less suitable solvents as defined above, hydrophilic surface-active agents, such as pegylated castor oil, polysorbate, and pegylated oils. The amount of the co-solvent may be determined according to the need, and may be, when present, from about 5% wt to 45% wt, preferably from about 10% wt to 30% wt. Water may also be used, particularly to assist the incorporation of salts, and/or to improve the biocompatibility. When used, the amount of water in the composition may be readily determined such that it does not cause the precipitation of the polymers. Usually, the amount of water needed to assist the incorporation of salts, e.g. calcium chloride, magnesium chloride, and calcium acetate, is between 0.5% wt and 20% wt, preferably between 1% wt and 15% wt, more preferably between 4% wt and 10% wt.

The additional excipients may decrease the viscosity of the composition or facilitate its administration. The additional excipients include, but not limited to, at least one of oils, such as castor oil, sesame oil, peanut oil, dibutyl phthalate, acetyl tributyl citrate, isopropyl myristrate or dibutyl sebacate; salts, permeation enhancers, such as acetate salts or bases. Suitable acetate salts are, e.g. sodium acetate, calcium acetate or ammonium acetate. Suitable bases are alkali hydroxides, e.g. sodium hydroxide, potassium hydroxide or ammonium hydroxide, or weak acid salts, e.g. acetates, carbonates, tri-phosphates and the like. The amount of the additional excipients may be determined according to the need, and may be, when present, from about 1% wt to 35% wt each, preferably less than 25% wt total additional excipients.

The additional excipients include, but not limited to, at least one additive substantially insoluble in the organic solvent. The solid additives may be added to impart specific properties to the solidified residue, e.g. positive charge and/or biocompatibility. The solid additives, e.g. particles may be of any suitable size, preferably smaller than 150 micrometers (μm), further preferably smaller than 100, 50, 25 or 10 μm, and include also nano-sized particles. The particular matter may comprise calcium or magnesium source as defined below, hydroxyapatite, gelatin, collagen, and a dispersed active agent. The amount of the dispersed matter may be, if present, according to the need from about 1% wt to about 30% wt, preferably from about 2% wt to 10% wt.

The polyvalent ion sources may release suitable ions, e.g. cations, upon contact with aqueous medium and/or upon solidification of the composition. The preferred ion sources are salts, which may preferably be chosen according to solubility in the preferred solvents of the compositions, optionally in presence of water as cosolvent. When released, the polyvalent cations may affect the permeability of the solidified residue, by interacting with the functional groups of the polymethacrylates, either with the quaternary ammonium groups or with the carboxylic acid groups. The interaction may results in temporary cross-linking of the polymer strands, decreasing the permeability and/or decreasing the dissolution rate of the polymers in the solid residue, and/or accelerating the solidification. Suitable polyvalent cation sources include, but not limited to calcium chloride, calcium phosphate, calcium acetate, magnesium chloride, sodium triphosphate, potassium triphosphate, sodium sulfate, or combinations thereof. Preferred polyvalent ion source is calcium chloride, used with methacrylic acid copolymers, and trisodium phosphate used with ammonio-methacrylates. The sufficient amount of the polyvalent ion source, if present, is according to the need, from about 2% eq to about 30% eq of the quaternary ammonium groups, and preferably from 30% eq to 1000% eq of carboxylic acid groups.

However, higher amounts of ion sources may also be present. Without being bound by a theory it is believed that the presence of salts in the solidifying matrix decreases solubility of the polymers as water starts penetration into the implant composition, thus increasing the precipitation rate of the polymers. Therefore, salts suitable for the compositions of the present invention may include monovalent ions, e.g. sodium, potassium, chloride, acetate, and others. Suitable salts include calcium chloride, magnesium chloride, sodium chloride, sodium citrate, calcium citrate, magnesium citrate, calcium acetate, magnesium acetate, a potassium phosphate, a sodium phosphate, a sodium potassium phosphate, and a combination of at least two of the above. Preferably, the salt is calcium chloride, calcium acetate or magnesium chloride.

Sometimes, more than one ion source may be used. Polyvalent ions may be present together with monovalent ions in the same implant, according to the need. A combination of polyvalent and/or monovalent ions may also be used according to need.

The total amount of salts may be between 1 and 10 weight percent, preferably between 3 and 6 weight percent.

The polymethacrylates may thus be formulated to bear a positive charge or to assume the positive charge upon solidification.

A composition may further comprise at least one active agent to form a medicated injectable barrier implant. The active agent may preferably be a bone-active active agent. The bone-active active agents include, but not limited to at least one of a statin, e.g. simvastatin, lovastatin, or atorvastatin; a cannabinoid, e.g. cannabidiol; a protein, e.g. a bone morphogenic protein (BMP); and/or a bisphosphonate, e.g. alendronate. The medicated implant may also comprise general active agents, in addition to or independently of the bone-active active agents. The general active agents include, but not limited to antibiotics, antifungals, antivirals, antineoplastics, antiepileptics, antiparkinsonics, and hormones.

The medicated implant may also comprise active agents suitable for oral or dental applications. These include antiseptics, antibiotics, antibiofilm agents, anti-quorum sensing agents, and a non-steroid anti-inflammatory agents (NSAIDs). Suitable antiseptics include, e.g. chlorhexidine, triclosan and cetyl pyridinium chloride. Suitable antibiotics include e.g. a tetracycline, e.g. doxycycline, and metronidazole. Suitable NSAIDs include, e.g. ibuprofen and flurbiprofen.

In some preferred embodiments, the injectable implant compositions comprise at least one solvent, at least one polymethacrylate, and at least one additive. Preferably, the solvent is N-methyl pyrrolidone, dimethyl sulfoxide, PEG 400, or combinations thereof. Preferably, the polymethacrylate is a copolymer of ethyl acrylate, methyl methacrylate and trimethylammonioethyl methacrylate chloride. Preferably, the additive is calcium chloride. The composition further comprises water, as a co-solvent. Preferably, the weight ratio between the polymethacrylate and calcium chloride is between 20:1 to 4:1, further preferably between 10:1 and 5:1. The concentration of polymethacrylate in the composition is preferably between 20% wt and 30% wt.

In some alternative preferred embodiments, the injectable implant compositions comprise at least one solvent, at least one first polymethacrylate, at least one second polymethacrylate, and optionally at least one additive. Preferably, the solvent is N-methyl pyrrolidone, dimethyl sulfoxide, PEG 400, or combinations thereof. Preferably, the first polymethacrylate is a copolymer of ethyl acrylate, methyl methacrylate and trimethylammonioethyl methacrylate chloride. Preferably, the second polymethacrylate is a copolymer of methacrylic acid and methyl methacrylate, or of methacrylic acid and ethyl acrylate. The additive, when present, is preferably calcium chloride. The composition further comprises water, as a co-solvent. Preferably, the weight ratio between the polymethacrylates and calcium chloride is between 20:1 to 5:1, further preferably between 15:1 to 7:1. Preferably, the weight ratio between the first polymethacrylate and the second polymethacrylate is between 10:1 to 1:1, further preferably between 7:1 to 2:1. The concentration of polymethacrylates in the composition is preferably between 10% wt and 25% wt.

In some alternative preferred embodiments, the injectable implant compositions comprise at least one solvent, at least one first polymethacrylate, at least one second polymethacrylate, and optionally at least one additive. Preferably, the solvent is N-methyl pyrrolidone, dimethyl sulfoxide, PEG 400, or combinations thereof. Preferably, the first polymethacrylate is a copolymer of dimethylaminoethyl methacrylate, butyl methacrylate, and methyl methacrylate, and the second polymethacrylate is a copolymer of methacrylic acid and methyl methacrylate, or of methacrylic acid and ethyl acrylate. The additive, when present, is preferably calcium chloride. Preferably, the weight ratio between the polymethacrylates and calcium chloride is between 100:1 to 10:1, further preferably between 25:1 to 15:1. Preferably, the weight ratio between the first polymethacrylate and the second polymethacrylate is between 10:1 to 1:2, further preferably between 7:1 to 1:1. In these embodiments the composition is preferably free of water. The concentration of polymethacrylates in the composition is preferably between 10% wt and 20% wt.

Upon solidification, the drug, e.g. bone-active agent, is released from the implant into the ambient aqueous medium. The release rate of the drug is retarded by the polymers of the solidified residue and is therefore controlled. Generally, the release rate may be adjusted to effect the controlled release of over 80% of the loaded drug or of the maximal deliverable dose at the desired time interval. The time interval is usually referred to as duration of the release, or even interchangeably with the term "release rate". Therefore, the term "release rate of 24 hours" should be construed as "controlled release at a rate to deliver at least 80% of the maximum deliverable dose in about 24 hours". Preferably, the initial burst release of the drug is lower than about 50% of the maximal deliverable dose, more preferably less than about 40% and less than about 30%.

The drug may be released by passive diffusion through the polymers' matrix, by erosion of the matrix, by diffusion via pores formed in said matrix, or by a mixed mechanism. The erosion mechanism is more applicable for the methacrylic acid copolymers as they gradually dissolve in the medium, whereas the diffusion may be more relevant in the ammonio-methacrylate copolymers. Mixed mechanism may be obtained by blending the polymers, and by addition of various additives, as described above. Usually, the release duration of the drug from the solid residue may be about 24 hours in vitro, sometimes about 36, 48, 60 or 72 hours, and may be also 1, 2, 3 or 4 weeks, depending on the nature of the drug and the solid residue, and the testing conditions.

Thus the release of the drug, e.g. of the bone-active agent, or a systemic agent, or an oral agent, may be controlled by the composition of the implant, particularly of the solidified implant. Generally, the weight fraction of the drug (also known as drug loading) may increase the release rate in absence of additional effects, e.g. saturation of the matrix or precipitation of the drug in the matrix. Depending on the nature of the release mechanism, the acceleration of the release may be achieved by addition of hydrophilic additives or by the agents increasing permeability of the matrix, e.g. acetate salt in ammonio-methacrylates; further retardation of the release may be achieved by addition of hydrophobic additives, by creating interactions between the polymeric components, e.g. blending ammonio-methacrylate copolymers and methacrylic acid copolymers, or by addition of polyvalent ions. Additionally, improving homogeneity (phase unification) of the solid residue may retard the release, whereas increasing the porosity or general polyphase structure may accelerate the release rate of the drugs. Additionally, increasing the polymer contents in the compositions may retard the release of drug from solidified implant. Finally, co-solvents may influence the release rate along the same lines as described above.

The release studies are conducted in a suitable dissolution medium. As both degradation of the implant and the drug release kinetics may be influenced by the volume and the nature of the dissolution medium, and as the proper in-vivo conditions are generally unknown, the dissolution medium volume should be chosen preferably to maintain sink conditions while limiting the dissolution of the residue for the tested time interval. The medium should be an aqueous buffered solution of pH about 7.2-7.7, preferably 7.4-7.5. Additionally, surface-active agents may be added to maintain sink conditions, as known in the art.

Generally, the viscosity of the compositions of implants or of the medicated implants allows injection via a medical needle or a comparable cannula. The viscosity may vary, for example, from 10 to 190 millipascal-seconds (mPa*s) for larger-gauge equipment, and from 50 to about 2500 mPa*s for smaller-gauge equipment, at a suitable injection rate. For example, for injection via a standard 19G gauge at rate 100 µL/s viscosities up to 2300 mPa*s may result in injection pressure of about 1000 mBar, and viscosity of about 415 mPa*s may result in injection pressure of about 180 mBar, at 250 µL/s the viscosity values of about 920 mPa*s and about 165 mPa*s result in the above pressure values. For a standard 23G needle the values may be 160 mPa*s for about 1000 mBar and about 30 for about 180 mBar for 100 µL/s injection rate, and 65 mPa*s and about 12 mPa*s for 250 µL/s. The maximal suitable viscosity may readily be calculated by the skilled artisan from the dimensions of the needle/catheter and the flow rate. Compositions may be tested using conventional rheometry apparatus and viscosity determined at shear rate relevant to the particular injection equipment.

The compositions of the barrier implants and of the medicated barrier implants of the present invention possess bone-adhesive properties. The polymethacrylates as described herein were shown to interact in solution with hydroxyapatite and bind onto it. This effect has been demonstrated in ethanolic solutions of Eudragit™ RL, wherein the concentration of the polymer in the solution decreased with increased amount of hydroxyapatite in dispersion, as described in greater detail in the Examples below. Without being bound by theory it is believed that the osteoadhesive potential may be beneficial for covering the fracture hematoma and/or damaged periosteum.

The compositions of the injectable implants may be prepared as known in the art. Briefly, the components soluble in a solvent are dissolved together, and when two or more solvents are present, the solutions of the dissolved components are combined together. For example, composition comprising a polymethacrylate copolymer and calcium chloride, may be prepared by dissolving separately calcium chloride in minimal amount of water and diluting it with comparable volume of the organic solvent, e.g. N-methyl pyrrolidone. The polymer is then dispersed in the remainder of the solvent, and mixed till dissolution, optionally under gentle heating. The hydro-organic solution of calcium chloride is then introduced into the polymer solution and mixed to homogeneity. If an active agent is present in the composition, e.g. simvastatin, it may be dissolved separately in the organic solvent, or concomitantly with the polymer.

Additionally, provided is a kit for extemporaneous preparation of the composition or of the medicated composition according to the invention, the kit comprising at least two separate containers comprising each at least one solvent or solution or at least one powder, such that upon aseptic addition of the solvent or solution to the powder a composition or a medicated composition of the invention is obtained. For example, one container may comprise the powder of a polymethacrylate or a mixture of polymethacrylates. Additionally or alternatively, a container may comprise an additive or a mixture of additives. Additionally or alternatively, a container may comprise a drug or a mixture of drugs. Additionally or alternatively, a container may comprise a solvent or a mixture of solvents.

In an additional aspect provided a method of treatment of bone fractures by administering to the patient in need a dose of composition or of medicated composition of the invention, perifracturally.

The administration of the composition or of the medicated composition may be preceded or followed by administration of auxiliary compositions, comprising at least one of a drug, a polyvalent ion, a cell, and/or a thermosensitive polymer solution.

The administration of the composition or of the medicated composition may be used to treat oral or dental diseases and conditions, such as root canals sterilization, implants placement procedures, periodontal pockets treatment, periodontal sulcus treatment, pericoronitis, mucositis, and dry socket. Additionally or alternatively, the composition or of the medicated composition may be used in adjunction to various oral procedures, e.g. extractions, oral surgery, cosmetic dentistry, teeth restoration, orthodontic procedures, filling the spaces between teeth, filling the spaces between or under surgical appliances, and denture placement.

The administration of the composition or of the medicated composition may be used to treat diseases or conditions in a patient in need thereof. The diseases or conditions include bacterial infections, fungal infections, viral infections, neoplasms, parkinsonism, e.g. Parkinson's disease, epilepsy, and hormonal conditions.

EXAMPLES

Methods

Weighing was performed with the accuracy to the designated significant number. Weighing deviation of no more than 2% was deemed acceptable. Temperature control other than at 37° C. was performed using benchtop oven, at 37° C. a heat room was used. Cooling was done in cold room set to 4° C.

Cetyl pyridinium chloride was determined by HPLC. Briefly, Hypersil® CN column, 150×4.6 mm, 5 µm, was used. CPC was eluted at 1 mL/min with methanol buffered with 20% of potassium dihydrogen phosphate 3 mM solution at pH 5. Injection volume was 100 µL. Concentrations were determined versus a calibration curve between 1.56 and 200 µg/mL. Detection was with UV at 260 nm.

Chlorhexidine was determined by HPLC. Briefly, 50 µL of specimens were eluted at 1 mL/min on Intersil ODS 80A® 150×4.6 mm column, 5 µm, with Metaguard 4.5 mm Intersil pre-column, with acetonitrile buffered with 60% of sodium acetate 0.05 M buffer with heptane sulfonic acid, at pH 5.0. Concentrations were determined versus a calibration curve between 1.56 and 200 µg/mL. Detection was with UV at 260 nm.

Simvastatin was determined by HPLC. Briefly, 50 µL of specimens were eluted at 1 mL/min on LiChrosphere® 100 RP18 125×4.6 mm column, 5 µm, with LiChrosphere Cart pre-column, with acetonitrile buffered with 35% of sodium dihydrogen phosphate 20 mM buffer, at pH 4.5. Concentrations were determined versus a calibration curve between 1.78 and 200 µg/mL. Detection was with UV at 238 nm.

Ibuprofen was determined by HPLC. Briefly, 50 µL of specimens were eluted at 1 mL/min on LiChrosphere® 100 RP18 250×4.6 mm column, 5 µm, with LiChrosphere Cart pre-column, with acetonitrile buffered with 60% of water acidified with 0.1% of phosphoric acid. Concentrations were determined versus a calibration curve between 1.56 and 200 µg/mL. Detection was with UV at 214 nm.

Doxycycline was determined by HPLC. Briefly, 100 µL of specimens were eluted at 1 mL/min on LiChrosphere® 100 RP18 250×4.6 mm column, 5 µm, with LiChrosphere Cart pre-column, with acetonitrile buffered with 70% of potassium dihydrogen phosphate 20 mM buffer, at pH 6.0. Concentrations were determined versus a calibration curve between 1.56 and 200 µg/mL. Detection was with UV at 245 nm.

Triclosan was determined by HPLC. Briefly, 100 µL of specimens were eluted at 1 mL/min on LiChrosphere® 100 RP18 150×4.6 mm column, 5 µm, with LiChrosphere Cart pre-column, with methanol buffered with 20% of ammonium acetate 0.01 M buffer. Concentrations were determined versus a calibration curve between 0.78 and 50 µg/mL. Detection was with UV at 280 nm.

Metronidazole was determined by HPLC. Briefly, 50 µL of specimens were eluted at 1 mL/min on LiChrosphere® 100 RP18 150×4.6 mm column, 5 µm, with LiChrosphere Cart pre-column, with acetonitrile buffered with 70% of potassium dihydrogen phosphate 10 mM buffer, at pH 4.7. Concentrations were determined versus a calibration curve between 0.78 and 100 µg/mL. Detection was with UV at 317 nm.

Preparation 1—Aqueous Gels

Poloxamers were obtained from BASF, as Lutrol® products. Non-sterile phosphate-buffered saline and calcium/magnesium fortified phosphate-buffered saline was prepared as described in Lichtenauer et al, Science Labmedicine, 40 (5), May 2009, doi:10.1309/LMBMG5A7NOVQBXWD. Briefly, monobasic potassium phosphate and potassium chloride, 200 mg each, and sodium chloride, 8.00 g, as well as dibasic sodium phosphate heptahydrate, 2.16 g, were dissolved in about 1 liter of double-distilled water, and brought to volume. For calcium/magnesium fortified PBS, 100 mg of each of calcium chloride and magnesium chloride hexahydrate were added per each liter and mixed till dissolution.

Poloxamer 407 and poloxamer 188 were dissolved at 4° C. The amounts are summarized in the table 1 below:

TABLE 1

|  | 1.1 | 1.2 | 1.3 | 1.4 | 1.5 | 1.6 | 1.7 | 1.8 |
|---|---|---|---|---|---|---|---|---|
| Poloxamer 407 | 25% | 30% | 20% | 25% | 25% | 30% | 30% | 20% |
| Poloxamer 188 |  |  | 10% |  |  |  |  | 10% |
| PBS |  |  |  | 75% |  | 70% |  |  |
| PBS+/+ |  |  |  |  | 75% |  | 70% | 70% |
| DDW | 75% | 70% | 70% |  |  |  |  |  |

The solutions remained liquid on cold, but rapidly gelled between 25° C. and 37° C. The degradation kinetics was assessed gravimetrically. Briefly, about 50 µL of gelled solution were diluted with amounts between 500-2500 µL of fresh medium. The gels dissolved within several changes of the medium, but no later than 48 hours.

Example 1—Osteoadhesion Potential of Eudragit® RL Polymer

Eudragit® RL was obtained from Evonik®. Ethanolic solutions were prepared by dissolving the indicated amounts of polymer in ethanol. Calcium hydroxyapatite was obtained from Sigma, was washed in ethanol to remove extractable materials and dried at 60° C. overnight prior to use.

About 0.6 g of Eudragit® RL were dissolved in about 100 mL of ethanol. The solution was marked as "0.5%". About 2 g of Eudragit® RL were dissolved in about 100 mL of ethanol. The solution was marked as "2%". About 5.5 g of Eudragit® RL were dissolved in about 100 mL of ethanol. The solution was marked as "5%". Aliquots of about 20 mL of the solutions were transferred into 50-mL centrifuge tubes, and amounts of about 300 mg, 600 mg and 900 mg of washed calcium hydroxyapatite were added to each. The powder was dispersed in Vortex for about 5 minutes and was left standing for about 1 hour, with occasionally stirring at Vortex mixer. Thereafter, the tubes were centrifuged at 4,000 rpm for about 20 minutes. The supernatant was assayed gravimetrically for the solids content.

TABLE 2

| initial | 300 mg | 600 mg | 900 mg |
|---|---|---|---|
| 0.50% group | | | |
| 0.56% | 0.39% | 0.31% | 0.20% |
| 2% group | | | |
| 2.39% | 2.27% | 1.81% | 1.73% |
| 5% group | | | |
| 6.64% | 6.31% | 5.75% | 5.56% |

Disposable Petri dishes were accurately weighed, thereafter about 4-5 grams of centrifuged solutions were added. The solutions were then dried overnight at 60° C. The results are summarized in the table 2 above.

A decrease in polymer concentration is observed. The results indicate that the polymer interacts with hydroxyapatite and deposits thereon, thus indicating that it may have adhesion potential to hydroxyapatite.

Example 2—Sterilizing the Polymers

Eudragit® polymers of RL, RS, L and S types were subjected to heating at 155-160° C. in a laboratory oven over two hours in a glass Petri dish. Thereafter, the dishes were closed with a cover and cooled to room temperature. In all polymers some melting/degradation was observed. The residue was dissolved in ethanol and cast onto tissue culture 6-well dishes, and dried in biological hood. The residues were washed with sterile PBS over 24 hours, and filled with DMEM growth medium, supplemented with 10% of FBS, sodium pyruvate and penicillin-streptomycin. No growth was observed after 96 hours.

Eudragit® RL was then tested calorimetrically at 160° C. isotherm, using differential scanning calorimetry. No events were detected. Upon heating, water evaporation peak was prominent feature, and upon cooling a glass transition temperature at about 120° C. could be discerned. This signifies that Eudragit® RL polymer can be sterilized with dry heat.

Alternatively, Eudragit® RL solutions were prepared in ethanol as in Example 2, cast into tissue culture plates, ca. 12 cm in diameter, and evaporated in the biological hood. The film was detached in the hood, and ground in a mortar, cleaned with 70% ethanol. The powder was dispersed in growth medium; no growth was observed after 96 hours.

Example 3—Solutions in Organic Liquids

Aliquots of Eudragit® RL, ca. 1 g, were slowly added under vortexing into 20-mL scintillation vials containing ca. 10 mL solvents as shown in the table below. The dispersions were left standing over weekend, with occasional vortexing. The dispersions were visually inspected to determine dissolution.

The obtained solutions were injected via 16G needle into PBS−/− and PBS+/+, preheated to 37° C. Solidification processes were visually observed.

The results are summarized in the Table 3 below. "Soluble" indicates clear solution of varying viscosity, "gelled" indicates clear saturated gel with liquid fraction, "insoluble" indicates presence of undissolved powder that remained after heating to 60° C. for 2 hours.

TABLE 3

| # | Solvent | Result |
|---|---|---|
| 4.1 | N-methyl pyrrolidone | Soluble |
| 4.2 | Dimethyl sulfoxide | Soluble |
| 4.3 | Polyethylene glycol 400 | Soluble |
| 4.4 | Polyethylene glycol 300 | Soluble |
| 4.5 | Triethyl citrate | Soluble |
| 4.6 | Glycerol | Soluble |
| 4.7 | Methoxypropylene glycol 350 | Soluble |
| 4.8 | Diethyl phthalate | Soluble |
| 4.9 | Propylene glycol | Soluble when hot |
| 4.10 | Dibutyl phthalate | Gelled |
| 4.11 | Tween 20 | Gelled |
| 4.12 | Tween 80 | Insoluble |
| 4.13 | Glyceryl triacetate | Insoluble |
| 4.14 | Acetyl tributyl citrate | Insoluble |
| 4.15 | Polyethylene glycol 200 | Insoluble |
| 4.16 | Span 20 | Insoluble |
| 4.17 | Span 80 | Insoluble |
| 4.18 | Isopropyl myristate | Insoluble |
| 4.19 | Dibutyl sebacate | Insoluble |

Dissolution kinetics was variable. For example, 4.1 and 4.2 dissolved almost instantaneously, whereas 4.9 had to be heated to 60° C. to dissolve. Solidification was variable as well. For example, 4.8 did not solidify at all, as the solvent is immiscible per se with water. Some formulations dispersed soon after solidification.

Example 4—Eudragit® Polymers in NMP and PEG 400—Viscosity

To determine the most suitable solvent for polymethacrylates, solutions in NMP and PEG 400 were prepared as follows. The weighed amount of the polymer was slowly added into the solvent inside 20-mL scintillation vial, under Vortex mixing, dispersed for ca. 1-2 minutes, then heated for about 15-30 minutes at 40° C. in an oven. The formulations prepared are shown in the table 4 below. Apparent viscosities are given as comparative subjective scale between 1 and 10. Gelled compositions are indicated as "G".

TABLE 4

| | Eudragit® RL | | | | | Eudragit® RS | | | | | Eudragit® L100 | | | | | Eudragit® S | | | | |
|---|---|---|---|---|---|---|---|---|---|---|---|---|---|---|---|---|---|---|---|---|
| NMP | 5 | 3.5 | 2.5 | 1.5 | 0 | 5 | 3.5 | 2.5 | 1.5 | 0 | 5 | 3.5 | 2.5 | 1.5 | 0 | 5 | 3.5 | 2.5 | 1.5 | 0 |
| PEG 400 | 0 | 1.5 | 2.5 | 3.5 | 5 | 0 | 1.5 | 2.5 | 3.5 | 5 | 0 | 1.5 | 2.5 | 3.5 | 5 | 0 | 1.5 | 2.5 | 3.5 | 5 |
| Solids 10% | 1 | 3 | 3 | 4 | 5 | 1 | 2 | 2 | 4 | 6 | 1 | 3 | 5 | 6 | 7 | 1 | 2 | 3 | 4 | 6 |
| Solids 20% | 2 | 5 | 9 | 10 | G | 2 | 4 | 5 | 7 | 9 | 3 | 4 | 7 | G | G | 3 | 4 | 6 | 8 | 9 |
| Solids 30% | 5 | 8 | 10 | G | G | 4 | 7 | 7 | G | G | 6 | 7 | 9 | G | G | 5 | 6 | 9 | G | G |

Formulations in NMP were tested at varying shear rate recording shear stress with rotary Anton Paar rheometer equipped with spindle S25. The viscosities in mPa*s at representative shear rates are given in the table 5 below.

TABLE 5

| | Eudragit® RL | | | Eudragit® RS | | | Eudragit® L100 | | | Eudragit® S | | | Eudragit® E | | |
|---|---|---|---|---|---|---|---|---|---|---|---|---|---|---|---|
| | Solids % | | | | | | | | | | | | | | |
| Shear rate | 10 | 20 | 30 | 10 | 20 | 30 | 10 | 20 | 30 | 10 | 20 | 30 | 10 | 20 | 30 |
| $2\ s^{-1}$ | 15.6 | 35.2 | 369 | 34.9 | 2.7 | 246 | 52.3 | 921 | 34K | 37.6 | 639 | 19K | 9.4 | 13.5 | 136 |
| $10\ s^{-1}$ | 16.9 | 67.2 | 342 | 10.6 | 42.3 | 253 | 70.3 | 915 | 33K | 41.5 | 646 | 18K | 6.8 | 36.3 | 149 |
| $50\ s^{-1}$ | 15.1 | 67.7 | 337 | 9.0 | 43.6 | 256 | 62.5 | 916 | 32K | 41.2 | 646 | 17K | 7.4 | 35.4 | 164 |
| $100\ s^{-1}$ | 14.5 | 68.0 | 338 | 9.1 | 44.0 | 258 | 63.4 | 922 | 30K | 39.9 | 659 | 17K | 8.1 | 52.1 | 306 |
| $150\ s^{-1}$ | 15.1 | 68.8 | 340 | 9.2 | 43.3 | 262 | 63.9 | 92.5 | 28K | 39.7 | 665 | 16K | 7.5 | 43.2 | 178 |
| $200\ s^{-1}$ | 14.5 | 69.8 | 343 | 8.6 | 43.9 | 266 | 64.3 | 926 | 26K | 39.0 | 668 | 15K | 8.2 | 43.7 | 172 |
| $250\ s^{-1}$ | 14.8 | 69.8 | 344 | 8.2 | 45.2 | 271 | 63.7 | 925 | 24K | 39.0 | 672 | 15K | 9.6 | 43.8 | 166 |
| $300\ s^{-1}$ | 15.0 | 70.0 | 347 | 9.6 | 42.9 | 274 | 64.7 | 923 | 23K | 37.2 | 679 | 14K | 9.1 | 40.1 | 164 |
| Comp.# | 4.20 | 4.21 | 4.22 | 4.23 | 4.24 | 4.25 | 4.26 | 4.27 | 4.28 | 4.29 | 4.30 | 4.31 | 4.32 | 4.33 | 4.34 |

It can be seen that although some formulations are pseudoplastic gels, others exhibit acceptable viscosity with mildly dilatant behavior, which in higher shear rates may cause structure breakdown and acceptable viscosity values at injection-relevant shear rates.

Example 5—Immersions and Solidification

Compositions were coated on glass cover slips or microscope slides, and these were immersed into PBS−/− and PBS+/+. About 100 µL were applied onto #2 20-mm cover slip, and about 300 µL were applied onto standard rectangular microscope slide. Formation and degradation of the residues was observed. Alternatively, the compositions were taken up in a syringe and injected via a 19G needle into ca 10-mL aliquots of the solutions n 20-mL scintillation vials, followed by mixing at Vortex mixer. Solidification and resilience to agitation was visually evaluated.

Cross-linked gelatin gels were prepared by addition of diluted glutaraldehyde solution (1:10) about 2.5% w/v, to gelatin solution. Diluted glutaraldehyde solution was prepared by diluting 25% w/v solution for microscopy, in distilled water. Briefly, about 5 g of bovine gelatin were dissolved at heating in ~100 mL of double-distilled water and chilled to room temperature. Aliquots of ~10 mL were placed into 20-mL scintillation vials. About 250 µL of diluted GA solution were added dropwise over ca. 1 minute, into the vial during mixing with Vortex. The gels were allowed to set over weekend.

Compositions were injected with a glass syringe equipped with 19G needle into the gel, about 200-300 µL. Formation and/or degradation of the residues was observed. A representative photograph of composition 5.1 is demonstrated in the FIG. 1.

Generally, calcium chloride was weighed into a 20-mL scintillation vial, followed by water, and swirled gently to dissolution. About 5.0 g of NMP were then added, and Eudragit® polymers were then added at Vortex, mixed for about 2 minutes. The rest of NMP per formulas was added, and the vials were left standing at 40° C. until dissolution (about 30 minutes). Composition 5.5 was prepared by dissolving separately Eudragit® L100 and Eudragit® E in about half of the required weight of NMP, and the solutions were combined at Vortex mixing, and tested immediately. The compositions (in grams) are shown in the tables 6 and 7.

TABLE 6

| | 5.1 | 5.2 | 5.3 | 5.4 | 5.5 | 5.6 | 5.7 | 5.8 | 5.9 |
|---|---|---|---|---|---|---|---|---|---|
| Eudragit® RL | 2.0 | 2.0 | | | | 2.0 | 2.0 | 2.0 | 1.0 |
| Eudragit® RS | | | 2.0 | 2.0 | | | | | |
| Eudragit® S100 | | | | | | 0.5 | | 0.5 | |
| Eudragit® L100 | | | | | 1.0 | | | | |
| Eudragit® EPO | | | | | 1.0 | | | | |
| Calcium chloride | 0.20 | 0 | 0.2 | 0 | 0 | 0.4 | 0.4 | 0 | 0.2 |
| DDW | 0.5 | | 0.5 | | | 0.8 | 0.8 | 0.8 | 0.4 |
| NMP | 7.3 | 7.5 | 7.3 | 7.5 | 8.0 | 6.4 | 6.4 | 6.8 | 8.4 |

TABLE 7

|  | 5.10 | 5.11 | 5.12 | 5.13 | 5.14 | 5.15 | 5.16 |
|---|---|---|---|---|---|---|---|
| Eudragit ® RL | 3.0 | 2.0 |  | 2.5 | 2.5 | 2.5 | 2.5 |
| Eudragit ® S100 |  | 0.5 |  |  |  |  |  |
| Eudragit ® L100 |  |  | 2.0 |  |  |  |  |
| Eudragit ® EPO |  |  | 1.0 |  |  |  |  |
| Additive amount | 0.30 | 0.3 |  | 0.3 | 0.3 | 0.3 | 0.3 |
| Additive | CaCl$_2$ | CaCl$_2$ |  | MgCl$_2$ | CaAc$_2$ | NaCit | NH$_4$Ac |
| DDW | 0.5 | 0.8 |  | 0.5 | 0.5 | 0.5 | 0.5 |
| NMP | 6.3 | 6.5 | 7.0 | 6.5 | 6.5 | 6.5 | 6.5 |

In the table 7:
CaCl$_2$ - calcium chloride,
MgCl$_2$ - magnesium chloride as hexahydrate,
CaAc$_2$ - calcium acetate,
NaCit - trisodium citrate as dihydrate,
NH$_4$Ac - ammonium acetate Compositions 5.2, 5.4 and 5.8, disintegrated shortly after solidification upon contact with aqueous medium, forming dispersed particulate matter of irregular form. Composition 5.9 was washed off from the slide while immersion. The other compositions were retained for 24-48 hours. Compositions 5.10-5.12 remained visually intact for at least 3 months at room temperature.

Example 6—Simvastatin Formulations

Simvastatin was formulated into the solidifying compositions. The compositions were prepared along the lines of the Example 5. Generally, simvastatin stock solution of about 15-20% wt in NMP was prepared, and calculated aliquots were added to the compositions according to the formula, upon dissolution of all polymers. The compositions (in mg) are shown in the table 8.

Figure 2:
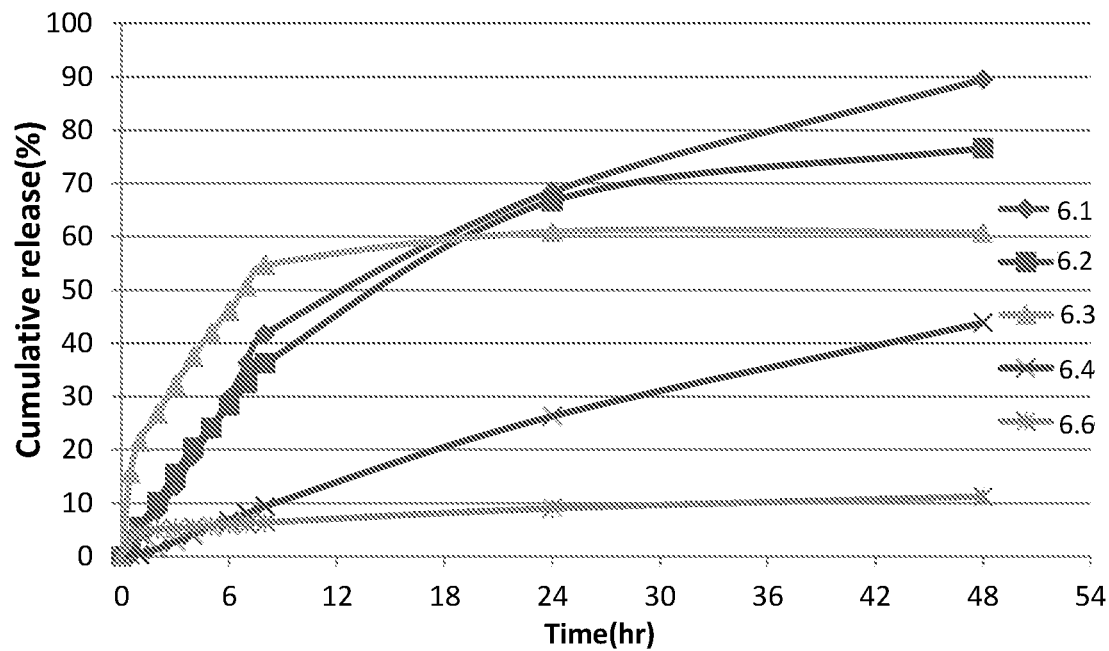
FIG. 2 demonstrates the release profiles of simvastatin from some of the injectable implant compositions of the invention.

The compositions were injected into 2.5 mL of tromethamine buffer at pH 6.8, augmented with 0.5% of SLS. About 100 μL of compositions were injected via 19G or 16G needle. The weight injected was determined gravimetrically by weighing the syringes. At designated time points the solution was completely replaced with fresh medium, and simvastatin concentrations were determined by HPLC. The exemplary release data of the formulations 7.1-7.6 is demonstrated in the FIG. 2.

TABLE 8

|  | 6.1 | 6.2 | 6.3 | 6.4 | 6.5 | 6.6 |
|---|---|---|---|---|---|---|
| Simvastatin | 38.0 | 38.0 | 38.0 | 57.0 | 49.4 | 57.0 |
| Eudragit ® RL | 2000 | 2000 |  | 3000 | 2600 |  |
| Eudragit ® E |  |  | 1000.0 |  |  | 1500 |
| Eudragit ® L |  |  | 1000.0 |  |  | 1500 |
| PEG 3350 |  |  |  |  | 250.0 |  |
| Calcium chloride | 400.0 | 200.0 |  | 300.0 | 260.0 |  |
| DDW | 800.0 | 400.0 |  | 600.0 | 520.0 |  |
| NMP | ~6750 | ~7350 | ~7950 | ~6050 | ~6050 | ~6050 |

Composition 6.7 is comparative example with no additive. The solution was more viscous than composition 6.8, and disintegrated rapidly upon injection into the release medium. The dissolution samples were obtained by careful decantation of the liquid.

Further compositions are summarized in the table 9 below.

TABLE 9

|  | 6.7 | 6.8 | 6.9 | 6.10 | 6.11 |
|---|---|---|---|---|---|
| Simvastatin | 50.0 | 50.0 | 50.0 | 50.0 | 50.0 |
| Eudragit ® RL |  |  | 1000 | 200 | 200 |
| Eudragit ® RS | 2000 | 2000 |  |  |  |
| Eudragit ® L |  |  | 1000 | 1800 | 1800 |
| Calcium chloride | 0 | 300 | 300 | 300 | 900 |
| DDW | 500 | 500 | 500 | 500 | 1200 |
| NMP | ~7450 | ~7150 | ~7150 | ~7150 | ~7850 |
| Cumulative simvastatin release | | | | | |
| After 1 hour | 17 | 5 | 7 | 11 | 5 |
| After 4 hours | 36 | 14 | 19 | 27 | 14 |
| After 8 hours | 51 | 21 | 31 | 42 | 23 |
| After 24 hours | 70 | 45 | 55 | 64 | 40 |

The results clearly demonstrate that controlled release of simvastatin under sink conditions may be achieved from solid implants.

Example 7—Cetyl Pyridinium Chloride (CPC) Formulations

CPC was formulated into injectable implants. The compositions were prepared according to the general procedure described in the example 5. Dissolution was performed in 2.5 mL of phosphate buffer according to the USP, at pH 6.8. Release medium was completely changed between the samples to maintain sink conditions. The compositions are summarized in the tables 10 and 11 below.

Compositions 7.8 and 7.9 are comparative examples with no additive. The solutions disintegrated rapidly upon injection into the release medium. No dissolution samples were collected. Conversely, composition 7.4, containing even less polymer, solidified immediately and remained intact throughout the experiment and allowed drug release, in rapid but controlled manner Composition 7.10 contained even less polymer, yet remained solidified throughout the drug release period, but completely dissolved after 72 hours.

TABLE 10

|  | 7.1 | 7.2 | 7.3 | 7.4 | 7.5 | 7.6 | 7.7 |
|---|---|---|---|---|---|---|---|
| CPC | 50 | 25 | 15 | 50 | 50 | 50 | 50 |
| Eudragit ® RL | 3025 | 3075 | 3085 | 2000 | 4000 |  | 2500 |
| Eudragit ® RS |  |  |  |  |  | 4000 |  |
| Calcium chloride | 275 | 275 | 275 | 200 | 285 | 200 | 250 |
| DDW | 500 | 500 | 500 | 400 | 600 | 400 | 500 |
| NMP | 6150 | 6150 | 6150 | 7350 | 6250 | 7350 | 6700 |

TABLE 10-continued

|  | 7.1 | 7.2 | 7.3 | 7.4 | 7.5 | 7.6 | 7.7 |
|---|---|---|---|---|---|---|---|
| Cumulative CPC release (%) | | | | | | | |
| After 1 hour | 8 | 9 | 13 | 77 | 5 | 14 | 8 |
| After 4 hours | 19 | 21 | 31 | 88 | 14 | 25 | 17 |
| After 8 hours | 27 | 33 | 52 | 96 | 22 | 35 | 25 |
| After 24 hours | 31 | 38 | 59 | 100 | 26 | 39 | 28 |

TABLE 11

|  | 7.8 | 7.9 | 7.10 | 7.11 | 7.12 |
|---|---|---|---|---|---|
| CPC | 50 | 50 | 50 | 50 | 50 |
| Eudragit ® RL | 2500 | | | | 3000 |
| Eudragit ® RS | | 2500 | | | |
| Eudragit ® L | | | 500 | 1500 | |
| PEG 3350 | | | | | 500 |
| Calcium chloride | 0 | 0 | 275 | 750 | 275 |
| DDW | 500 | 500 | 500 | 1000 | 500 |
| NMP | 6950 | 6950 | 8675 | 6700 | 5675 |
| Cumulative CPC release (%) | | | | | |
| After 1 hour | NA | NA | 31 | 4 | 8 |
| After 4 hours | | | 93 | 34 | 17 |
| After 8 hours | | | 100 | 71 | 25 |
| After 24 hours | | | 101 | 92 | 28 |

TABLE 12

|  | 7.13 | 7.14 | 7.15 | 7.16 |
|---|---|---|---|---|
| CPC | 50 | 50 | 50 | 50 |
| Eudragit ® RL | 2025 | 1250 | 1500 | 400 |
| Eudragit ® L | 1000 | 650 | 400 | 1500 |
| Calcium chloride | 275 | 250 | 250 | 250 |
| DDW | 500 | 600 | 600 | 600 |
| NMP | 7825 | 7650 | 7200 | 7200 |
| Cumulative CPC release (%) | | | | |
| After 1 hour | 5 | 8 | 6 | 9 |
| After 4 hours | 14 | 20 | 18 | 42 |
| After 8 hours | 30 | 43 | 40 | 81 |
| After 24 hours | 56 | 66 | | 97 |

Further compositions are summarized in the table 12 above. Composition 7.16 swelled slightly during the release experiment, but remained solid.

The results clearly demonstrate that controlled release of CPC under sink conditions may be achieved from solid implants.

Example 8—Chlorhexidine (CHX) Formulations

Chlorhexidine digluconate and dihydrochloride were formulated into injectable implants. The compositions were prepared according to the general procedure described in the example 5. Dissolution was also performed in 2.5 mL of phosphate buffer according to the USP, at pH 6.8. Release medium was completely changed between the samples to maintain sink conditions. The compositions are summarized in the table 13 below.

Composition 8.2 is comparative example with no additive. The solution disintegrated rapidly upon injection into the release medium. The dissolution samples were obtained by careful decantation of the liquid.

TABLE 13

|  | 8.1 | 8.2 | 8.3 | 8.4 | 8.5 | 8.6 | 8.7 |
|---|---|---|---|---|---|---|---|
| CHX - diacetate | 100 | 100 | 25 | 25 | 100 | 200 | 25 |
| Eudragit ® RL | | | | 3075 | 2700 | 2700 | 4000 |
| Eudragit ® RS | 2000 | 3000 | 2700 | | | | |
| Calcium chloride | 200 | 0 | 270 | 287 | 250 | 250 | 287 |
| DDW | 400 | 400 | 500 | 500 | 500 | 500 | 500 |
| NMP | 6500 | 6700 | 6500 | 6150 | 6050 | 6000 | 5265 |
| Cumulative CHX release (%) | | | | | | | |
| After 1 hour | 68 | 89 | 57 | 52 | 41 | 46 | 29 |
| After 4 hours | 86 | 98 | 79 | 83 | 70 | 68 | 65 |
| After 8 hours | 95 | 99 | 88 | 94 | 81 | 81 | 80 |
| After 24 hours | 100 | 99 | 91 | 100 | 87 | 88 | 93 |

Further compositions are summarized in the tables 14-15 below.

TABLE 14

|  | 8.8 | 8.9 | 8.10 | 8.11 | 8.12 | 8.13 | 8.14 | 8.15 |
|---|---|---|---|---|---|---|---|---|
| CHX - diacetate | 25 | 25 | 25 | 25 | 25 | 25 | 25 | 300 |
| Eudragit ® RL | 1700 | 1450 | 2200 | 200 | 200 | 100 | 400 | 1700 |
| Eudragit ® L | 1000 | 850 | 500 | 1800 | 1800 | 1900 | 1600 | 1000 |
| Calcium chloride | 270 | 230 | 270 | 300 | 900 | 900 | 900 | 270 |
| DDW | 500 | 500 | 500 | 500 | 1200 | 1200 | 1200 | 500 |
| NMP | 6505 | 6945 | 6505 | 8175 | 11075 | 8685 | 8685 | 6230 |
| Cumulative CHX release (%) | | | | | | | | |
| After 1 hour | 7 | 8 | 12 | 15 | 17 | 18 | 13 | 2.9 |
| After 4 hours | 17 | 18 | 31 | 39 | 59 | 73 | 58 | 3.5 |
| After 8 hours | 31 | 31 | 54 | 68 | 94 | 114 | 94 | 4.0 |
| After 24 hours | 43 | 52 | 68 | 81 | 98 | 121 | 100 | 4.3 |

Various effects in the combination of constitutively positively charged polymer (Eudragit® RL) and negatively ionizable polymer (Eudragit® L) demonstrate that a variety of release profiles may be obtained. All the solidified residues remained solid and did not degrade throughout the experiment.

TABLE 15

|  | 8.16 | 8.17 | 8.18 | 8.19 |
|---|---|---|---|---|
| CHX—(HCl)$_2$ | 50 | 25 | 25 | 25 |
| Eudragit ® RL | 3000 | 1700 | 2300 | 2500 |
| Eudragit ® L | | 1000 | 400 | 200 |
| Calcium chloride | 275 | 270 | 270 | 270 |
| DDW | 500 | 500 | 500 | 500 |
| NMP | 6150 | 6505 | 6505 | 6505 |
| Cumulative CHX release (%) | | | | |
| After 1 hour | 45 | 13 | 14 | 11 |
| After 4 hours | 81 | 23 | 23 | 16 |
| After 8 hours | 94 | 36 | 34 | 12 |
| After 24 hours | 102 | 45 | 39 | 12 |

The results also suggest that the release profile may be tuned with the loading of the drug, and with its salt. The results clearly demonstrate that controlled release of CHX under sink conditions may be achieved from solid implants.

Example 9—Antimicrobial Activity of CPC and CHX Formulations

To test the efficacy of solidified residues on live bacteria, the residues of compositions 7.4, 7.13, and 8.3 were solidified on agar plate. The solidification was performed as follows: polypropylene tubes of ca 6 mm in diameter were segmented into 2-mm pieces, sterilized and placed onto standard agar plates (5.2% BHI Agar)(Neogen Corporation, Lansing, Mich., USA). An aliquot of about 30 μL was introduced with a syringe and 23-G needle into the thus-formed reservoir. The contact of the compositions with the agar surface led to solidification creating a smooth and uniform surface. In order to solidify the rest of the solution, 9 mL of sterile phosphate buffered saline (PBS)(Sigma Aldrich, USA) were added with great care to the agar plate (Miniplast, Ein-Shemer, Israel) to assure the complete immersion of the cylindrical residues. The aqueous medium was removed after 10 min and the solidified residues were used immediately for the experiment.

*E. faecalis* V583 from a stock solution was diluted (1:100) in 5 mL of Brain Heart Infusion (BHI) media (Neogen Corporation, Lansing, Mich., USA) for an overnight growth in a shaking incubator at 37° C. The bacterial culture was adjusted to $OD_{600}$~0.07. Glucose was added to a final concentration of 2% to enhance biofilm formation.

From the adjusted bacterial culture above, 100 μl were spread on BHI Agar plates. Four replicates of the residues, prepared as described above, were placed on seeded agar plates. After 24 hours, the zone of inhibition (ZOI) for each formulation was measured in $mm^2$ with the free software Digimizer (v4.6.1, MedCalc Software), and the residues were transferred with sterilized tweezers to new agar plates. The procedure was repeated every 24 hours until no significant ZOI could be observed.

The ZOI was very high after 24 h for 8.3 and 7.4 samples, but drastically decreased during the following days. The residue of 7.13 did not show a large initial ZOI, nevertheless there was only a relatively small and continuous decrease in the ZOI for the following days. The residue of 8.3 had a significant ZOI after 4 days and the antibacterial activity of the residue of 7.13 lasted for 3 days.

To evaluate the effect of the residues on the biofilm formation, cell culture plates with 48-wells (CCPs) (SPL Life Sciences co., Ltd. Korea) of polystyrene were used. Aliquots of 270 μL of the bacterial culture were introduced into each well. Then, the solidified residues of 7.4, 7.13, 8.3, and their placebo residues, i.e. residues from formulations identical in terms of the polymers and other excipients but devoid of CPC and CHX, respectively, were introduced into the wells. The bacterial culture was replaced with fresh culture every 24 h for a defined time period, until biofilm was formed.

Biofilm formation was assessed with tetrazolium reduction test over time. In the same experiment, quantitative polymerase chain reaction test and count of colony-forming units, were performed to measure planktonic cells.

Figure 3:
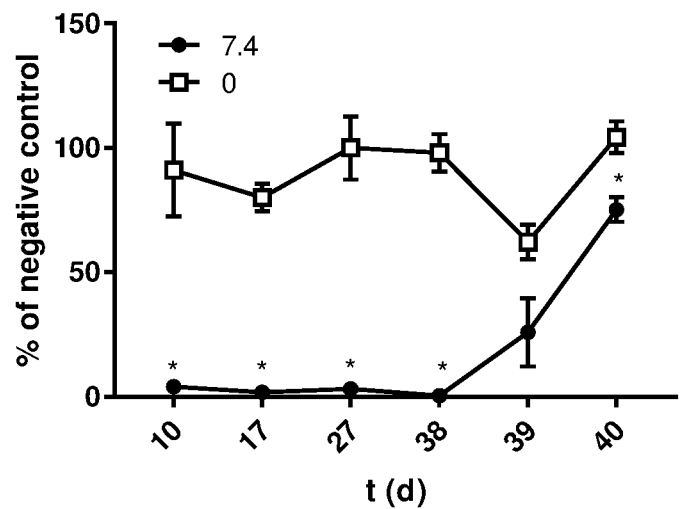
FIG. 3 demonstrates the bacterial inhibition by a solidified residue from an injectable implant according to the invention, as seen by bacterial metabolic activity.

Tetrazolium reduction test (MTT test) was performed as follows: after the removal of the residues, the wells were washed twice with 200 μL of phosphate-buffered saline (Sigma-Aldrich) solution to remove planktonic cells. Then 50 μL of 0.1% w/v dimethylthiazol-2-yl)-2,5-diphenyltetrazolium bromide (i.e. MTT) (Calbiochem, Germany) was added to cover the biofilm completely. After one hour of incubation at 37° C., the excess of MTT was removed with 150 μL of sterile PBS. To dissolve the reduced tetrazolium salts contained in the biofilm, 150 μl of dimethyl sulfoxide (DMSO, Biolab, Israel) was added to each well and the plate was placed on an orbital shaker (S-3.02.10M, ELMI Ltd.) for 10 min at room temperature. Aliquots of 100 μl of the solubilized MTT solution were transferred to new wells on a 96-well plate and absorbance measured at 570 nm with a reference length of 620 nm with the help of a spectrophotometric plate reader (Infinite 200 PRO, Tecan Trading AG, Switzerland). The results of MTT assay for the residue are shown in the FIG. 3. In the Figure, solid circles show the results of the formulation 7.4 (designated "7.4"), and the empty squares the results of placebo (designated "0"). The time in days is designated in the X-axis caption "t(d)".

Quantitative PCR was performed as follows. DNA was isolated from the supernatant fluid of tested samples; aliquots of 40 μL were added to 160 μL of 0.05M solution of NaOH (Daejung, Korea). The test tubes containing the sample and NaOH were heated in a waterbed for 60 min at 60° C. to effect cell lysis. After this, 18.5 μL of 1M solution of TRIS (pH=7) was added to the tubes to avoid further degradation of the DNA. The obtained DNA was stored at −20° C. and subsequently used as template for qPCR analysis.

Figure 4:
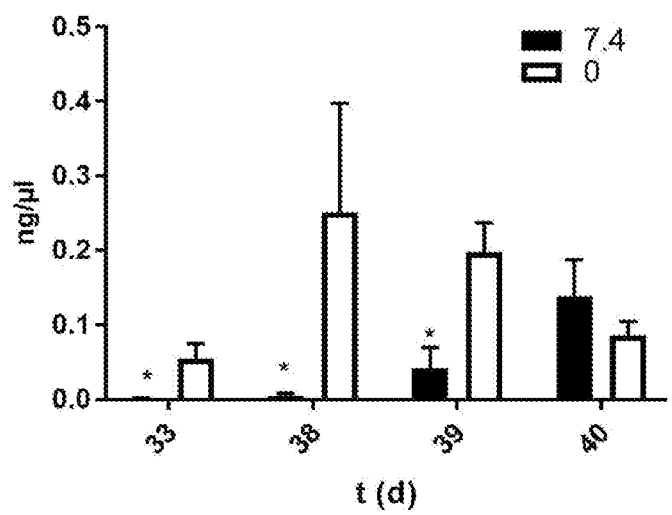
FIG. 4 demonstrates the bacterial inhibition by a solidified residue from an injectable implant according to the invention, as seen by quantitative polymerase chain reaction analysis.

Specific primers F=5' CGTTCTTTCCTCCCGAG 3' and R=5' GCCATGCG-GCATAAACTG 3' were used to target the 16s rRNA gene of *E. faecalis*. SYBR green dye (Power Sybr Green PCR Master Mix, ThermoFisher Scientific) was added to detect amplicons. The qPCR was performed in ABI-Prism 7300 Instrument (Applied Biosystems, Foster City, Calif., USA), and quantification was performed versus calibration curve. Purified DNA for the calibration was obtained from overnight bacterial cultures of *E. faecalis*, obtained using the GenElute Bacterial Genomic DNA kit (Sigma-Aldrich, USA), according to the protocol provided by the manufacturer. The results of qPCR of the supernatant are shown in the FIG. 4. In the Figure, solid bars show the results of the formulation 7.4 (designated "7.4"), and the empty bars the results of placebo (designated "0"). The time in days is designated in the X-axis caption "t(d)", and the DNA concentrations on the Y-axis are designated in "ng/μL".

Figure 5:
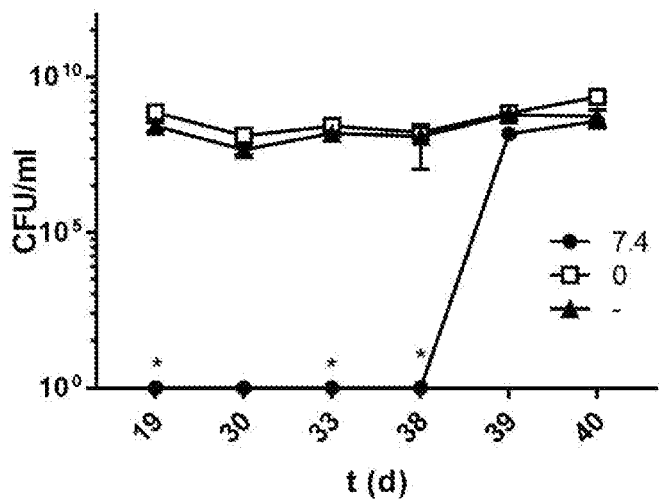
FIG. 5 demonstrates the bacterial inhibition by a solidified residue from an injectable implant according to the invention, as seen by bacterial counts.

Colony forming units count was performed to quantify the number of viable planktonic cells in the supernatant fluid. Aliquots of 50 μL of supernatant fluid were spread on BHI Agar plates, at different 10-fold dilutions factors, and incubated overnight in aerobic conditions at 37° C. The CFU were counted with the free software Digimizer. The results of CFU count for the 7.4 residues are shown in the FIG. 5. In the Figure, solid circles show the results of the formulation 7.4 (designated "7.4"), empty squares the results of placebo (designated "0"), and the solid triangles the negative control (designates with a negative sign "−"). The time in days is designated in the X-axis caption "t(d)".

Bacterial cultures exposed to 7.4 residues did not develop any viable biomass for 38 days. Certain growth was apparent on day 39, and there was no difference between the test and the control at day 40. The residues of 7.13 and 8.3 inhibited *E. faecalis* growth for 3 days. Interestingly, for all residues tested, bacterial cultures exposed to the placebo showed a significant increase in biofilm formation on the third day in relation to the negative control, which may be related to the reaction of the polymer matrix itself. After the third day this situation was reversed, and biofilm formation in all placebo samples decreased in relation to negative control.

Example 10—Ibuprofen Formulations

Ibuprofen was formulated into injectable implants. The compositions were prepared according to the general procedure described in the example 5. Dissolution was also performed in 2.5 mL of phosphate buffer according to the USP, at pH 6.8. Release medium was completely changed between the samples to maintain sink conditions. The compositions are summarized in the table 16 below.

TABLE 16

|  | 10.1 | 10.2 | 10.3 | 10.4 | 10.5 | 10.6 | 10.7 |
|---|---|---|---|---|---|---|---|
| Ibuprofen | 50 | 50 | 50 | 50 | 50 | 50 | 50 |
| Eudragit ® RL | 2000 | 2000 | 3000 |  |  | 1500 | 1800 |
| Eudragit ® RS |  |  |  | 2500 | 2500 |  |  |
| PEG 400 |  | 500 |  |  |  |  |  |
| Calcium chloride | 300 | 250 | 300 | 0 | 350 | 300 | 500 |
| DDW | 400 | 500 | 600 | 500 | 500 | 400 | 600 |
| NMP | 7250 | 6750 | 6050 | 6950 | 6600 | 7750 | 7050 |

TABLE 16-continued

|  | 10.1 | 10.2 | 10.3 | 10.4 | 10.5 | 10.6 | 10.7 |
|---|---|---|---|---|---|---|---|
| Cumulative ibuprofen release (%) | | | | | | | |
| After 1 hour | 15 | 10 | 6 | 49 | 15 | 30 | 5 |
| After 4 hours | 29 | 20 | 10 | 68 | 22 | 52 | 11 |
| After 8 hours | 37 | 27 | 13 | 76 | 26 | 64 | 17 |
| After 24 hours | 46 | 35 | 18 | 78 | 31 | 69 | 24 |

Further compositions are summarized in the table 17 below.

TABLE 17

|  | 10.8 | 10.9 | 10.10 | 10.11 | 10.12 | 10.13 | 10.14 |
|---|---|---|---|---|---|---|---|
| Ibuprofen | 50 | 50 | 50 | 50 | 50 | 50 | 50 |
| Eudragit ® RL | 1500 | 1000 |  | 1000 | 1000 |  |  |
| Eurdagit ® RS |  |  | 1000 |  |  | 1000 |  |
| Eudragit ® L | 1500 | 1000 | 1000 | 1000 | 1000 | 1000 | 900 |
| Eudragit ® E |  |  |  |  |  |  | 900 |
| Calcium chloride | 250 | 250 | 250 | 160 | 100 | 160 | 0 |
| DDW | 500 | 500 | 500 | 500 | 500 | 500 | 0 |
| NMP | 6200 | 7200 | 7200 | 7290 | 7350 | 7290 | 8150 |
| Cumulative ibuprofen release (%) | | | | | | | |
| After 1 hour | 4 | 4 | 12 | 25 | 31 | 34 | 53 |
| After 4 hours | 8 | 10 | 26 | 37 | 48 | 56 | 75 |
| After 8 hours | 14 | 15 | 39 | 47 | 60 | 66 | 88 |
| After 24 hours | 26 | 29 | 55 | 65 | 77 | 69 | 91 |

Composition 10.4 is comparative example with no additive. The solution disintegrated rapidly upon injection into the release medium. The dissolution samples were obtained by careful decantation of the liquid. Incomplete release may be due to adsorption onto and into powdered polymer. The composition 10.5, vis-à-vis 10.4, solidified immediately and remained intact, releasing low amounts of ibuprofen over time.

It can also be seen that compositions 10.14 remains intact, although contain no salt additive, but consist instead of two methacrylate copolymers of opposite nature: a carboxylic methacrylate and an amino methacrylate.

The results clearly demonstrate that controlled release of ibuprofen under sink conditions may be achieved from solid implants.

Example 11—Doxycycline Formulations

Doxycycline was formulated into injectable implants. The compositions were prepared according to the general procedure described in the example 5. Dissolution was also performed as for ibuprofen in example 10 above. The compositions are summarized in the table 18 below.

TABLE 18

|  | 11.1 | 11.2 | 11.3 | 11.4 | 11.5 | 11.6 | 11.7 | 11.8 | 11.9 | 11.10 |
|---|---|---|---|---|---|---|---|---|---|---|
| Doxycycline | 50 | 50 | 50 | 50 | 50 | 50 | 50 | 50 | 50 | 50 |
| Eudragit ® RL | 3000 | 2000 | 2200 | 1450 | 1000 | 1450 | 1668 |  | 500 | 750 |
| Eudragit ® L |  | 1000 | 500 | 850 | 2000 | 850 | 978 | 1200 | 1000 | 1500 |
| Eudragit ® E |  |  |  |  |  |  |  | 1200 |  |  |
| Calcium chloride | 275 | 275 | 270 | 230 | 270 | 500 | 265 |  | 250 | 250 |
| DDW | 500 | 500 | 500 | 500 | 500 | 900 | 500 |  | 500 | 500 |
| NMP | 6175 | 6175 | 6480 | 6920 | 6480 | 6250 | 6540 | 7550 | 7700 | 6950 |
| Cumulative doxycycline release (%) | | | | | | | | | | |
| After 1 hour | 46 | 27 | 36 | 31 | 26 | 56 | 36 | 48 | 47 | 40 |
| After 4 hours | 79 | 41 | 57 | 49 | 43 | 70 | 48 | 65 | 65 | 56 |
| After 8 hours | 89 | 52 | 72 | 67 | 55 | 83 | 59 | 73 | 74 | 66 |
| After 24 hours | 93 | 65 | 85 | 82 | 63 | 91 | 73 | 78 | 81 | 77 |

It can be seen that composition 11.8 remains intact, although contain no salt additive, but consist instead of two methacrylate copolymers of opposite nature: a carboxylic methcrylate and an amino methacrylate.

The results clearly demonstrate that controlled release of doxycycline under sink conditions may be achieved from solidifying implants.

Example 12—Triclosan Formulations

Triclosan was formulated into injectable implants. The compositions were prepared according to the general procedure described in the example 5. Dissolution was also performed as for ibuprofen in example 10 above. The compositions are summarized in the tables 19 and 20 below.

TABLE 19

|  | 12.1 | 12.2 | 12.3 | 12.4 | 12.5 | 12.6 | 12.7 | 12.8 |
|---|---|---|---|---|---|---|---|---|
| Triclosan | 50 | 50 | 50 | 50 | 50 | 50 | 50 | 50 |
| Eudragit ® RL | 2000 | 1000 | 1000 | 1250 | 1250 | 1500 | 1900 | 1900 |
| Eudragit ® L |  | 1000 | 1000 | 750 | 750 | 500 | 100 | 100 |
| Calcium chloride | 300 | 250 | 160 | 250 | 500 | 250 | 250 | 500 |
| DDW | 400 | 500 | 500 | 500 | 750 | 500 | 500 | 750 |
| NMP | 7250 | 7250 | 7290 | 7250 | 6700 | 7250 | 7250 | 6700 |
| Cumulative triclosan release (%) | | | | | | | | |
| After 1 hour | 51 | 3 | 2 | 3 | 3 | 5 | 11 | 2 |
| After 4 hours | 61 | 7 | 4 | 5 | 10 | 10 | 16 | 4 |
| After 8 hours | 62 | 22 | 11 | 10 | 15 | 17 | 19 | 6 |
| After 24 hours | 63 | 28 | 15 | 30 | 18 | 32 | 19 | 6 |

Further compositions are summarized in the table 20 below.

TABLE 20

|  | 12.9 | 12.10 | 12.11 | 12.12 | 12.13 |
|---|---|---|---|---|---|
| Triclosan | 50 | 50 | 50 | 50 | 50 |
| Eudragit ® RL |  |  |  | 1000 |  |
| Eurdagit ® RS | 2500 | 2000 | 2000 | 1000 |  |
| Eudragit ® L |  |  |  |  | 1000 |
| Eudragit ® E |  |  |  |  | 700 |
| Calcium chloride |  | 250 | 750 | 250 |  |
| DDW | 500 | 500 | 1000 | 500 |  |
| NMP | 6950 | 7200 | 8200 | 7200 | 8250 |
| Cumulative triclosan release (%) | | | | | |
| After 1 hour | NA | 5 | 26 | 13 | 21 |
| After 4 hours |  | 6 | 27 | 15 | 23 |
| After 8 hours |  | 8 | 30 | 17 | 26 |
| After 24 hours |  | 8 | 30 | 17 | 26 |

Further compositions are summarized in the table 21 below.

TABLE 21

|  | 12.14 | 12.15 | 12.16 | 12.17 | 12.18 | 12.19 | 12.20 | 12.21 |
|---|---|---|---|---|---|---|---|---|
| Triclosan | 50 | 50 | 50 | 50 | 50 | 50 | 50 | 50 |
| Eudragit ® RL | 850 | 700 | 1000 | 1000 | 1000 | 1000 | 1000 | 1000 |
| Eudragit ® L | 850 | 700 | 1000 | 1000 | 1000 | 1000 | 1000 | 1000 |
| Methocel ® 5LV |  |  | 500 | 300 | 150 |  |  |  |
| Klucel ® EF |  |  |  |  |  | 300 |  |  |
| Kollidon ® 30 |  |  |  |  |  |  | 500 |  |
| Kollidon ® VA64 |  |  |  |  |  |  |  | 500 |
| Calcium chloride | 250 | 250 | 250 | 250 | 250 | 250 | 300 | 300 |
| DDW | 500 | 500 | 500 | 500 | 500 | 500 | 500 | 500 |
| NMP | 7500 | 7800 | 6700 | 6900 |  |  |  |  |
| Cumulative triclosan release (%) | | | | | | | | |
| After 1 hour | 8 | 11 | 6 | 7 | 7 | 8 | 6 | 8 |
| After 4 hours | 15 | 17 | 15 | 16 | 17 | 18 | 18 | 27 |
| After 8 hours | 36 | 35 | 32 | 33 | 38 | 43 | 56 | 56 |
| After 24 hours | 57 | 43 | Gelled* | 52 | 65 | 75 | 87 | 91 |

*Gelled - the release medium gelled and could not be separated.

Various effects may be seen from the formulations. Without being bound by a theory it is believed that the permeability of triclosan to Eudragit® RL is low, as seen by the arrest of drug release in formulations with high content of the polymer. The solidification kinetics is apparently highly accelerated by the second polymer, and by the amount of salt.

Composition 12.9 is comparative example with no additive, versus 12.10. The solution disintegrated rapidly upon injection into the release medium. The dissolution samples were not collected. It can be seen that compositions 12.13 remains intact, although contain no salt additive, but consist instead of two methacrylate copolymers of opposite nature: a carboxylic methcrylate and an amino methacrylate. The same release arrest may be observed in 12.10 and in 12.13.

The compositions containing an additional polymer (cellulose derivatives, povidones) demonstrate improved release profiles. Without being bound by a theory it is believed that cellulose derivative entrapped in the solidifying polymer matrix leeches out rapidly and leaves pores that facilitate triclosan release. Moreover, the solubilizing nature of povidone polymers may further enhance the release rate, e.g. by local solubilization of triclosan in the pores.

The results clearly demonstrate that controlled release of triclosan under sink conditions may be achieved from solid implants.

Example 13—Metronidazole Formulations

Metronidazole was formulated into injectable implants. The compositions were prepared according to the general procedure described in the example 5. Dissolution was also performed as for ibuprofen in example 10 above. The compositions are summarized in the tables 22 below.

TABLE 22

|  | 13.1 | 13.2 | 13.3 | 13.4 | 13.5 | 13.6 | 13.7 | 13.8 |
|---|---|---|---|---|---|---|---|---|
| Metronidazole | 50 | 50 | 50 | 50 | 25 | 25 | 25 | 25 |
| Eudragit ® RL | 2000 |  | 500 |  |  | 400 | 1500 | 1800 |
| Eudragit ® RS |  | 2500 | 2500 |  |  |  |  |  |
| Eudragit ® L |  |  |  | 800 | 200 |  |  |  |
| Eudragit ® E |  |  |  | 800 | 1000 | 2000 | 500 | 200 |
| Calcium chloride | 300 |  | 300 |  |  | 600 | 250 | 250 |
| DDW | 400 | 500 | 500 |  |  | 900 | 500 | 500 |
| NMP | 7250 | 6950 | 9175 | 8350 | 8775 | 8000 | 7225 | 7225 |
| Cumulative metronidazole release (%) | | | | | | | | |
| After 1 hour | 105 | NA | 72 | 112 | 133 | 67 | 136 | 105 |
| After 4 hours | 113 |  | 90 | 118 | 136 | 82 | 146 | 121 |
| After 8 hours | 112 |  | 95 | 117 | 136 | 90 | 145 | 119 |
| After 24 hours | 112 |  | 98 | NP | 136 | 94 | 145 | 118 |

Further compositions are summarized in the table 23 below.

TABLE 23

|  | 13.8 | 13.9 | 13.10 | 13.11 | 13.12 | 13.13 | 13.14 |
|---|---|---|---|---|---|---|---|
| Metronidazole | 50 | 50 | 25 | 50 | 50 | 500 | 1000 |
| Eudragit ® RL | 1000 | 1000 | 1000 | 1000 | 1000 | 1000 | 1000 |
| Eudragit ® L | 1000 | 1000 | 1000 | 1000 | 1000 | 1000 | 1000 |
| Calcium chloride | 250 | 160 | 300 | 250 | 600 | 600 | 600 |
| DDW | 500 | 500 | 500 | 500 | 900 | 900 | 900 |
| NMP | 7250 | 7290 | 9175 |  |  | 6000 | 6500 |
| NMP:PEG 400, 1:1 |  |  |  | 7250 | 8450 |  |  |
| Cumulative metronidazole release (%) | | | | | | | |
| After 1 hour | 67 | 79 | 78 | 100 | 108 | 101 | 72 |
| After 4 hours | 81 | 95 | 96 | 132 | 129 | 114 | 96 |
| After 8 hours | 86 | 98 | 96 | 133 | 129 | 116 | 106 |
| After 24 hours | 86 | 98 | 97 | NP | NP | 116 | 107 |

Composition 13.2 is comparative example with no additive, versus 13.1 and 13.3. The solution disintegrated rapidly upon injection into the release medium. The dissolution samples were not collected. It can be seen that compositions 13.4 and 13.5 remain intact, although contain no salt additive, but consist instead of two methacrylate copolymers of opposite nature: a carboxylic methcrylate and an amino methacrylate. Despite that, the release was almost immediate, probably due to extremely high solubility of metronidazole in NMP and in water.

It can be seen from the results of compositions 13.8-13.14 that although some effect may be seen with such factors, as drug concentration, amount of salt, polymer concentration and solvent (metronidazole is less soluble in PEG 400 than in NMP), minimal effect is observed on the drug release.

Further compositions are summarized in the table 24 below. The compositions containing a gelling polymer, soluble in NMP (i.e. hypromellose) demonstrate slightly improved release profiles. Without being bound by a theory it is believed that cellulose derivative entrapped in the solidifying polymer matrix creates pores in the solidified matrix and increases the viscosity of the medium inside the pores, which assists in controlling metronidazole release. Additionally, polyethylene oxide was found to be easily dispersible in the polymer solution. The powder does not interfere with solidification, but creates strong gel upon contact with water.

TABLE 24

|  | 13.15 | 13.16 | 13.17 | 13.18 | 13.19 | 13.20 | 13.21 | 13.22 | 13.23 |
|---|---|---|---|---|---|---|---|---|---|
| Metronidazole | 25 | 25 | 500 | 500 | 500 | 500 | 500 | 500 | 500 |
| Eudragit ® RL | 500 | 500 | 200 | 200 | 1000 | 1000 | 1000 | 1000 | 1000 |
| Eudragit ® L |  |  | 1800 | 1800 | 1000 | 1000 | 1000 | 1000 | 1000 |
| Eudragit ® S | 2500 | 2500 |  |  |  |  |  |  |  |
| Methocel ® K15M |  |  |  |  | 500 |  | 150 |  |  |
| Methocel ® K100M |  |  |  |  |  | 500 |  | 150 |  |
| Polyox ® N60K |  |  |  |  |  |  |  |  | 150 |
| Calcium chloride | 300 | 600 | 900 | 300 | 300 | 300 | 300 | 300 | 300 |
| DDW | 500 | 900 | 1200 | 500 | 500 | 500 | 500 | 500 | 500 |
| NMP | 9175 | 8475 | 7850 | 6700 | 10200 | 10200 | 6700 | 6550 | 6550 |
| Cumulative metronidazole release (%) | | | | | | | | | |
| After 1 hour | 78 | 78 | 98 | 68 | 65 | 64 | 88 | 89 |  |
| After 4 hours | 93 | 95 | 113 | 90 | 106 | 107 | 112 | 119 |  |
| After 8 hours | 94 | 104 | 114 | 99 | 117 | 114 | 118 | 125 |  |
| After 24 hours | 94 | 109 | 114 | 102 | 119 | 115 | 119 | 126 |  |

The results indicate that controlled release of metronidazole under sink conditions may be achieved from solid implants.

Example 14—Compositions with Fillers

Compositions comprising soluble and insoluble fillers were prepared. Soluble filler was sodium chloride; insoluble filler was calcium hydroxyapatite. The compositions (in mg) are shown in the table 25.

Ethanol-washed calcium hydroxyapatite was used, as described in the Example 1.

Sodium chloride was dissolved in water in 20 mL scintillation vial; polymer solution in NMP was rapidly added therein under Vortex mixing. Coarse emulsion was observed. The composition was taken up fresh into a syringe and injected via 19G needle into pre-heated (40° C.) PBS-/-. Immediate solidification was observed.

TABLE 25

|  | 14.1 | 14.2 |
|---|---|---|
| Eudragit ® RL | 2000 | 2000 |
| Sodium chloride | 400 |  |
| DDW | 900 |  |
| Calcium hydroxyapatite |  | 400 |
| NMP | ~6700 | ~7600 |

Similarly, calcium hydroxyapatite was dispersed in a polymer solution in mortar with pestle, collected into the scintillation vial and mixed with Vortex. The composition was taken up fresh into a syringe and injected via 19G needle into pre-heated (40° C.) PBS-/-. Immediate solidification was observed.

Example 15—Solidification of Formulations in Animals

Solidification of the implants was tested in freshly sacrificed animals from an unrelated experiment. Two 40-kg female pigs were used. Compositions 7.4 and 7.8 served as model injections. Formulas that were kept at ambience for about 2 months were used. Aliquots of about 500 µL each, were slowly injected into thigh muscles, ca 15 minutes after the euthanasia was established. Two injections per animal were performed.

The carcasses were left unheated for about 30 minutes. Thereafter, the injection sites were surgically opened and the vicinity of the injection observed.

All the injection sites of 7.4 contained solidified implants. Conversely, the injection sites of 7.8 contained no solids. Residual liquid was observed between the muscle filaments.

These results indicate that the solidification seen in vitro may be indicative to the behavior of the compositions in living systems.

Example 16—MCF7 Adhesion—Films and Solidified Residues

As a proof of principle MCF7 cells were used and their ability to adhere and grow on solidified residues was tested. MCF7 cell line was cultured under aseptic conditions. Briefly, DMEM fortified with 10% fetal bovine serum, sodium pyruvate and streptomycin-penicillin was used as growth medium. Cells were grown on tissue culture dishes until confluence or slightly beyond, trypsinized, washed with fresh medium and seeded onto substrates in 6-well plates, about $3-4 \times 10^5$. After 72 hours the medium was removed, cells washed twice with PBS-/-, and cells stained with crystal violet on opaque substrates, or observed without staining on clear substrates.

Substrates were prepared as follows: To demonstrate the attachment of MCF7 cells to the Eudragit® RL polymer, the 6-well plates were coated with ethyl cellulose that does not support cells growth. The ethyl cellulose coating was slightly wetted with ethanol, and ca. 10 mg of polymer powder was gently sprayed over the surface. Upon evaporation of ethanol, the wells were washed with PBS, dried, and sterilized under UV for 2 hours.

To demonstrate the attachment of MCF7 cells to solidified substrates, Eudragit® ethanolic solutions were cast onto Petri dishes and dried in biological hood. The films were removed and ground in mortar washed in 70% ethanol. NMP was sterilized by filtration through Nylon 0.45 µm filters. DMSO was supplied sterile and used as received. Scintillation vials were sterilized under UV for 2 hours. The solutions were prepared as follows: sterile polymer powder was added into the vial tared on analytical balances, and the vial was capped and weighed. The required amount of NMP was calculated from the density, and was added into the vial. The vial was mixed using Vortex until dissolution. The attachment experiments were performed with and without calcium chloride. Upon dissolution, aliquots of about 100 µL were placed onto round cover slips placed into the wells, and the wells were gently filled with PBS−/− or PBS+/+, mL The solvent was extracted for 2 hours, whereupon the cells were seeded in growth medium. After completion of the experiments, the cover slips were gently lifted and overturned to allow microscopy with bottom-objective apparatus.

Figure 6:
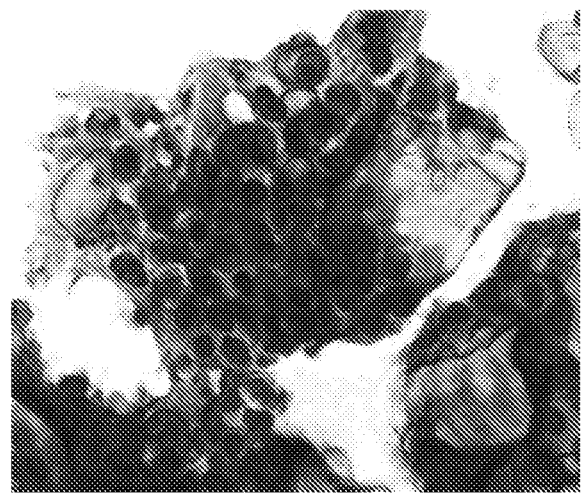
FIG. 6 demonstrates a micrograph of surrogate adhering cells adhering to a particle of ammoniomethacrylate copolymer USP.

The micrograph at ×40 magnification of MCF7 cells grown on Eudragit® RL powder is shown in the FIG. 6.

Particle is seen coated with MCF7 cells. White areas are ethyl cellulose transparent coating. It can be readily seen that no cells growth was observed in the ethyl cellulose substrate.

Figure 7:
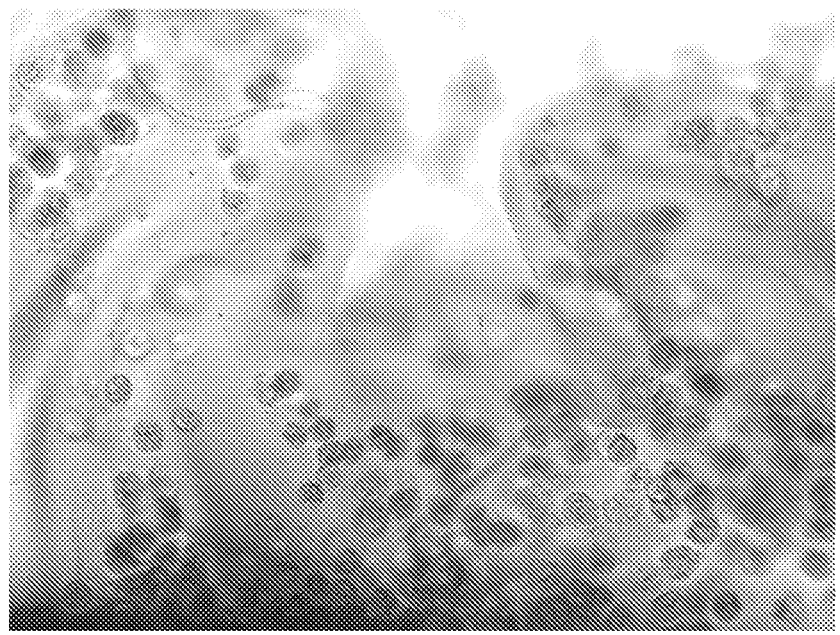
FIG. 7 a micrograph of surrogate adhering cells adhering to a solidified residue of an injectable implant of one embodiment of the invention.

The micrograph at ×40 magnification of MCF7 cells grown on Eudragit® RL solidified implant from NMP with calcium chloride is shown in the FIG. 7. The off-focus cells were observed due to uneven surface of the solidified implant.

We claim:

1. An injectable polymer-based implant composition comprising an ammonio-methacrylate copolymer said copolymer being dissolved in an injectable solvent, an additive which is a water-soluble salt, and optionally a pharmaceutically active agent, wherein upon contact with an aqueous medium polymer(s) of the implant composition form a stable solidified residue, and wherein said injectable solvent is soluble in or miscible with water and is an aprotic solvent, wherein said additive is a calcium-containing salt, and water is present in an amount between 0.5 and 20 weight percent.

2. The injectable implant of claim 1, wherein said aprotic polar solvent is selected from the group consisting of N-methyl pyrrolidone, dimethyl sulfoxide, and combinations thereof.

3. The injectable implant of claim 1, wherein the salt is calcium chloride.

4. The injectable implant of claim 1, further comprising a cosolvent, wherein said cosolvent is selected from the group consisting of polyols, organic acid esters, and pegylated hydrophilic surface active agents,
optionally wherein said polyols being polyethylene glycol with molecular weight between 300 and 4000, propylene glycol, or glycerine; and
optionally wherein said organic acid esters being triethyl citrate or diethyl phthalate.

5. The injectable implant of claim 1, further comprising a methacrylic acid copolymer, which is selected from copolymers of methacrylic acid and methyl methacrylate, and copolymers of methacrylic acid and ethyl acrylate.

6. The injectable implant of claim 1, wherein said ammonio methacrylate copolymer is a copolymer of ethyl acrylate, methyl methacrylate and trimethylammonioethyl methacrylate chloride.

7. The injectable implant of claim 1, further comprising an amino methacrylate copolymer, which is a copolymer of dimethylaminoethyl methacrylate, butyl methacrylate, and methyl methacrylate.

8. The injectable implant of claim 1, further comprising at least one further polymer, selected from the group consisting of a polyester, a cellulose derivative, polyvinyl pyrrolidone, a polyethylene glycol, a polyethylene oxide, and a poloxamer.

9. The injectable implant of claim 8, wherein said cellulose derivative is selected from the group consisting of methyl cellulose, hypromellose, and hydroxypropyl cellulose.

10. The injectable implant of claim 1, wherein the pharmaceutically active agent is bone-active agent, optionally wherein said bone-active agent is simvastatin.

11. The injectable implant of claim 1, wherein the pharmaceutically active agent is selected from the group consisting of antibiotics, antifungals, antivirals, antineoplastics, antiepileptics, antiparkinsonics, and hormones.

12. The injectable implant of claim 1, wherein the pharmaceutically active agent is an antiseptic or a non-steroid anti-inflammatory agent.

13. The injectable implant of claim 12, wherein the antiseptic is cetyl pyridinium chloride, or wherein said non-steroid anti-inflammatory agent is ibuprofen.

14. The injectable implant of claim 1, comprising a copolymer of ethyl acrylate, methyl methacrylate and trimethylammonioethyl methacrylate chloride as the ammoniomethacrylate copolymer, calcium chloride as an additive, water, a pharmaceutically active agent, and N-methyl pyrrolidone as said aprotic polar solvent.

15. The injectable implant of claim 14, further comprising a polymethacrylate selected from a copolymer of methacrylic acid and methyl methacrylate, a copolymer of methacrylic acid and ethyl acrylate, and a mixture thereof.

16. Method of accelerating a bone fracture healing in a patient in need thereof by administering perifracturally an injectable polymer-based implant composition comprising an ammonio-methacrylate copolymer, said copolymer being dissolved in an injectable solvent, an additive which is a water-soluble salt, and optionally a bone active agent, wherein upon contact with an aqueous medium polymer(s) of the implant form a stable solidified residue, and wherein said injectable solvent is soluble in or miscible with water and is an aprotic solvent, wherein said additive is a calcium-containing salt, and water is present in an amount between 0.5 and 20 weight percent.

17. The method of claim 16, wherein said injectable implant composition further comprises a copolymer of methacrylic acid and methyl methacrylate, a copolymer of methacrylic acid and ethyl acrylate, or a mixture thereof.

18. Method of treatment of a dental or an oral pathology in a patient in need thereof by administering to said patient an injectable polymer-based implant composition comprising an ammonio-methacrylate copolymer, said copolymer being dissolved in an injectable solvent, an additive which is a water-soluble salt, and a pharmaceutically active agent, wherein upon contact with an aqueous medium polymer(s) of the implant form a stable solidified residue, and wherein said injectable solvent is soluble in or miscible with water and is an aprotic solvent, wherein said additive is a calcium-containing salt, and
water is present in an amount between 0.5 and 20 weight percent.

19. The method of claim 18, wherein said pharmaceutically active agent selected from an antiseptic, an antibiotic, an antibiofilm agent, an anti-quorum sensing agent, and a non-steroid anti-inflammatory agent.

20. Method of treatment of a pathology in a patient in need thereof by administering to said patient intramuscularly, subcutaneously or intraperitoneally an injectable polymer-based implant composition comprising an ammoniomethacrylate copolymer, said copolymer being dissolved in an injectable solvent, an additive which is a water-soluble salt, and a pharmaceutically active agent, wherein upon contact with an aqueous medium polymer(s) of the implant form a stable solidified residue, and wherein said injectable solvent is soluble in or miscible with water and is an aprotic solvent wherein said additive is a calcium-containing salt, and water is present in an amount between 0.5 and 20 weight percent.

21. The injectable implant according to claim 1, wherein said water-soluble salt is selected from the group consisting of calcium chloride, calcium citrate, and calcium acetate.

22. The injectable implant according to claim 1, wherein said water-soluble salt is selected from the group consisting of calcium chloride and calcium acetate.

23. The injectable composition according to claim 1, wherein said amount of water is between 1 and 15 weight percent.

* * * * *